United States Patent [19]

Manning et al.

[11] Patent Number: 5,770,559
[45] Date of Patent: Jun. 23, 1998

[54] SOLUBILIZATION OF PHARMACEUTICAL SUBSTANCES IN AN ORGANIC SOLVENT AND PREPARATION OF PHARMACEUTICAL POWDERS USING THE SAME

[75] Inventors: Mark C. Manning, Fort Collins; Theodore W. Randolph, Niwot, both of Colo.; Eli Shefter, LaJolla, Calif.; Richard F. Falk, III, Boulder, Colo.

[73] Assignee: The Regents of the University of Colorado, Boulder, Colo.

[21] Appl. No.: 473,008

[22] Filed: Jun. 6, 1995

Related U.S. Application Data

[63] Continuation-in-part of Ser. No. 961,162, Oct. 14, 1992, abandoned.
[51] Int. Cl.$^6$ .............................. A61K 38/00; A23J 1/00
[52] U.S. Cl. ................................ 514/2; 514/21; 530/412; 530/418; 530/419; 530/427; 424/450; 424/489
[58] Field of Search .......................... 514/2, 21; 530/412, 530/418, 419, 427; 424/450, 489

[56] References Cited

U.S. PATENT DOCUMENTS

| | | | |
|---|---|---|---|
| 4,851,211 | 7/1989 | Adjei et al. ................................ | 424/40 |
| 4,897,256 | 1/1990 | Adjei et al. ................................ | 424/43 |
| 5,043,280 | 8/1991 | Fischer et al. ....................... | 435/235.1 |

FOREIGN PATENT DOCUMENTS

| | | |
|---|---|---|
| 0 275 404 | 7/1988 | European Pat. Off. . |
| 0 310 801 | 4/1989 | European Pat. Off. . |
| WO 90/0857 | 8/1990 | WIPO . |
| WO 94/08599 | 4/1994 | WIPO . |

OTHER PUBLICATIONS

Helenius et al., "Solubilization of Membranes by Detergents," Biochimica Biophysica Acta, 415 (1975) pp. 29–79, Elsevier Scientific Publishing Company, Amsterdam.
Dorin et al., "Recovering Refractile Bodies Containing Heterologous Proteins from Microbial Hosts and Their Use," Chemical Abstracts, 107:38079y (1987).
Zaks et al., "Enzymatic Catalysis in Nonaqueous Solvents," Journal of Biological Chemistry, vol. 263, No. 7 (Mar. 5, 1988) pp. 3194–3201, American Society for Biochemistry and Molecular Biology, Inc.
Abu–Hamidyyah et al., "General Anesthetic Agents and the Conformation of Proteins. 2. Strengthening of Hydrophobic Interaction in B–lactoglobulin by 1–alkanols and the cutoff effect in anesthetic potency," Chemical Abstracts, 110:205059n (1989).
Mazzenga et al., "The Transdermal Delivery of Zwitterionic Drugs I: the solubility of Zwitterionic Salts," Journal of Controlled Release, 16 (1991) pp. 77–88, Elsevier Science Publishers, Amsterdam.
Wells, et al., "Effect of Surfactants on Release of Highly Water–Soluble Medicinal Compound From an Inert, Heterogeneous Matrix," Journal of Pharmaceutical Sciences, vol. 81, No. 5 (May 1992) pp. 453–457, American Pharmaceutical Association.

Yeo, et al., "Formation of Microparticulate Protein Powder Using a Supercritical Fluid Antisolvent," Biotechnology and Engineering, vol. 41 (1993) pp. 341–346, John Wiley & Sons, Inc.
Randolph et al., "Sub–Micrometer–Sized Biodegradable Particles of Poly(L–Lactic Acid) via The Gas Antisolvent Spray Precipitation Process," Preprint, Biotechnology Progress 9 (Jul./Aug. 1993) pp. 429–435, American Chemical Society and American Institute of Chemical Engineers.
Powers et al., "Enhanced Solubility of Proteins and Peptides in Nonpolar Solvents Through Hydrophobic Ion Pairing," Biopolymers, vol. 33 (1993) pp. 927–932, John Wiley & Sons, Inc.
Matsuura et al., "Structure and Stability of Insulin Dissolved in 1–octanol," Journal of the American Chemical Society, vol. 115, No. 4, (1993) pp. 1261–1264, American Chemical Society.
Adjei et al., "Effect of ion–pairing on 1–octanol–water partitioning of peptide drugs. I: The nonapeptide leuprolide acetate," International Journal of Pharmaceutics, 90 (1993) pp. 141–149, Elsevier Science Publishers, Amsterdam.
Bromberg et al., "Detergent–Enabled Transport of Proteins and Nucleic Acids Through Hydrophobic Solvents," Proc. Nat'l. Acad. Sci. USA, vol. 91 (Jan. 1994) pp. 143–147.
Meyer et al., "Selective Precipitation of Interleukin–4 Using Hydrophobic Ion Paring: A Method for Improved Analysis of Proteins Formulated with Large Excesses of Human Serum Albumin," Pharmaceutical Research, vol. 11, No. 10 (1994) pp. 1492–1495, Plenum Publishing Corporation.
Meyer et al., "Solution Behaviour of α–Chymotrypsin Dissolved in Nonpolar Organic Solvents Via Hydrophobic Ion Pairing," Biopolymers, vol. 35 (1995) pp. 451–456, John Wiley & Sons, Inc.
Bromberg et al., "Transport of Proteins Dissolved in Organic Solvents Across Biomimetic Membranes," Proc. Nat'l. Acad. Sci. USA, vol. 92 (Feb. 1995) pp. 1262–1266.
Wells et al, *Journal of Pharmaceutical Science*, vol. 81, No. 5, pp. 453–457, 1992.
Zaks et al., *Journal of Biological Chemistry*, vol. 263, No. 7, pp. 3194–3201, 1988.
Abu Hamidiyyah et al, *Chemical Abstracts*, vol. 110, Ref. #205054n, 1989.

*Primary Examiner*—Cecilia J. Tsang
*Assistant Examiner*—Abdel A. Mohamed
*Attorney, Agent, or Firm*—Holme Roberts & Owen

[57] ABSTRACT

Provided is a method for preparing a true, homogeneous solution of a pharmaceutical substance dissolved in an organic solvent in which the pharmaceutical substance is not normally soluble. Solubilization is obtained by forming a hydrophobic ion pair complex involving the pharmaceutical substance and an amphiphilic material. The resulting organic solution may be further processed to prepare pharmaceutical powders. A biodegradable polymer may be co-dissolved with the pharmaceutical substance and the amphiphilic material and may be incorporated into a pharmaceutical powder. A preferred method for preparing pharmaceutical powders is to subject the organic solution to gas antisolvent precipitation using a supercritical gas antisolvent such as carbon dioxide. Also provided is a method for making hollow particles having a fiber-like shape which would provide enhanced retention time in the stomach if ingested by a human or animal host.

31 Claims, 18 Drawing Sheets

SOLUBILIZATION OF PHARMACEUTICAL SUBSTANCES IN AN ORGANIC SOLVENT AND PREPARATION OF PHARMACEUTICAL POWDERS USING THE SAME

CROSS-REFERENCE TO RELATED APPLICATIONS

This application is a continuation-in-part of U.S. patent application Ser. No. 07/961,162 filed on Oct. 14, 1992, now abandoned.

ACKNOWLEDGEMENT OF GOVERNMENT SUPPORT

This invention was made with government support under Grant No. BCS9157318 awarded by The National Science Foundation. The Government has certain rights in the invention.

FIELD OF THE INVENTION

The present invention relates to preparation of pharmaceutical formulations including liquid solutions and powders.

BACKGROUND OF THE INVENTION

Pharmaceutical substances may be introduced into a human or animal host for therapeutic or curative purposes in a number of ways. In many pharmaceutical applications, the pharmaceutical substance is administered in the form of solid particles. For example, a micropump may be used in some applications for prolonged treatment by slowly injecting a suspension of small particles in a liquid. Also, small particles having both a pharmaceutical substance and a biodegradable polymer may be placed within tissue for sustained release of the pharmaceutical substance, with the biodegradable polymer acting to control the release of the pharmaceutical substance. Furthermore, in pulmonary delivery applications, small particles may be inhaled to lodge in tissue of the lungs, permitting the pharmaceutical substance to then enter the circulatory system.

Often, however, problems are encountered in attempting to make particles having the desired properties for a particular pharmaceutical application. For example, when particles having a biodegradable polymer and a pharmaceutical substance are prepared, the pharmaceutical substance often concentrates near the surface of the particles. This effect may cause a sudden, undesirable release of the pharmaceutical substance when it is initially introduced into the host. Also, when using a micropump for continuous injection of a suspension over a prolonged period, the solid particles tend to settle over time, which may cause an undesirable variation in the rate of delivery of the pharmaceutical substance.

With respect to pulmonary delivery applications, current methods for delivering the pharmaceutical substance in small particles typically result in a majority of the pharmaceutical substance being wasted. In one method, called nebulization, a liquid having the pharmaceutical substance in solution is sprayed at a high velocity and inhaled. Alternatively, nebulization may involve spraying a powder as fine particles propelled by a carrier gas, with the particles being inhaled. Particles administered by both these nebulization methods, however, may have a wide distribution of droplet or particle sizes, resulting in a very low utilization of the pharmaceutical substance. Particles, or droplets, which are too large tend to lodge in the throat and mouth during inhalation and are not, therefore, effective for delivering the pharmaceutical substance to the lungs. Particles, or droplets, which are too small tend not to impact on the lung tissue, but rather tend to be exhaled. As much as 80 to 90 percent, or more, of the pharmaceutical substance may, therefore, be wasted and only a small portion of the pharmaceutical substance which is administered may actually reach the desired target in the lung.

Many of these problems with delivery of particles of a pharmaceutical substance result from limitations on methods used to make the particles. One method for making particles of a pharmaceutical substance, called lyophilization, involves rapid freezing of the pharmaceutical substance with water, followed by rapid dehydration of the frozen material to produce dry particles of the pharmaceutical substance. This technique has been used with proteins and other polypeptides, but the low temperatures involved may reduce the biological activity of some polypeptide molecules. Also, the particles produced by lyophilization tend to be large and clumping and are often not suitable for pharmaceutical delivery methods which require smaller particles. It is possible to grind the lyophilized particles to produce smaller particles, but such grinding may damage some pharmaceutical substances, especially proteins. Also, even when a substance may be ground without significant damage to the activity of the substance, it is difficult to obtain a pharmaceutical powder having particles of a narrow size distribution. Therefore, such pharmaceutical powders are prone to substantial waste of the pharmaceutical substance, such as described above for pulmonary delivery applications.

One method which has been proposed for making small particles of a pharmaceutical substance is called gas antisolvent precipitation. In this method, a pharmaceutical substance is dissolved in an organic solvent which is then sprayed into an antisolvent fluid, such as carbon dioxide, under supercritical conditions. The antisolvent fluid rapidly invades spray droplets, causing precipitation of very small pharmaceutical particles.

The gas antisolvent precipitation technique, however, requires that the pharmaceutical substance be soluble in the solvent. For hydrophobic pharmaceutical substances, this generally presents no problem because those substances can readily be dissolved in relatively mild, non-polar organic solvents. Hydrophilic pharmaceutical substances, however, are substantially insoluble in such relatively mild organic solvents.

It has been proposed that insulin, a hydrophilic protein, may be processed in a gas antisolvent precipitation process by dissolving the insulin in dimethylsulfoxide (DMSO) or N,N-dimethylformamide (DMF), both of which are strong, highly polar solvents. One problem with such a process, however, is that highly polar solvents such as DMSO and DMF tend to unfold protein molecules from their native tertiary structure, or conformation. These protein molecules would, therefore, also be precipitated in an unfolded state for incorporation into the solid particles. Such unfolding could seriously reduce the biological activity of a protein or other polypeptide, especially if stored as a solid particle in the unfolded state for any appreciable time.

There is a need for improved methods for making solid particles of pharmaceutical substances, and especially for making particles of hydrophilic substances, to permit preparation of particles having an appropriate size and size distribution without the molecular unfolding associated with the gas antisolvent precipitation method and without the low temperatures and grinding associated with lyophilization.

SUMMARY OF THE INVENTION

According to the present invention, a method is provided for placing a pharmaceutical substance into solution in an organic solvent in the form of a hydrophobic ion pair complex with an amphiphilic material. The resulting solution may then be subjected to gas antisolvent precipitation using a near critical or supercritical fluid to produce a precipitate of particles comprising the pharmaceutical substance. Particles may be produced with a relatively narrow size distribution in a variety of sizes, thereby permitting flexibility in preparing particles for effective utilization in a variety of pharmaceutical applications.

The present invention, therefore, permits pharmaceutical substances which are ordinarily substantially not soluble in an organic solvent to be solubilized, which facilitates further processing to prepare pharmaceutical powders. The method is particularly preferred for use with proteins and other polypeptide molecules. Those molecules may be dissolved in a relatively mild, relatively non-polar organic solvent, thereby reducing the potential for the reduction in biological activity which could result from use of a strong, highly polar is organic solvent were used in which the hydrophilic molecules are directly soluble.

In one embodiment of the present invention, a biodegradable polymer may be co-dissolved in the organic solvent along with the pharmaceutical substance and the amphiphilic material. When processed by gas antisolvent precipitation, the particles produced comprise an intimate mixture of the biodegradable polymer with the pharmaceutical substance and the amphiphilic material. Problems of compositional variation or concentration of the pharmaceutical substance near the surface of the particle are therefore, reduced relative to processes which require processing of a pharmaceutical substance in a suspension.

In another embodiment of the present invention, a pharmaceutical substance is provided having particles comprising a pharmaceutical substance and an amphiphilic material in a hydrophobic ion pair complex. In one embodiment, the particles have a narrow size distribution, with greater than about 90 weight percent of the particles having a size smaller than about 10 microns. In another embodiment, the solid particles are hollow and have a substantially elongated, fiber-like shape. These elongated particles are advantageous in that they should have a longer retention time, compared to substantially spheroidal particles, in the stomach of a human or animal host following ingestion. Therefore, the particles may be advantageously used for sustained release applications for delivery of a pharmaceutical substance in the stomach region.

In yet a further embodiment of the present invention, a method is provided for delivering a pharmaceutical substance for treatment of a human or animal host in which a pharmaceutical formulation is administered having solid particles including a pharmaceutical substance and an amphiphilic material. The administration may be by inhalation of the solid particles, by injection of a suspension of the solid particles in a liquid medium or by ingestion of the solid particles.

DETAILED DESCRIPTION OF THE INVENTION

Figure 1:
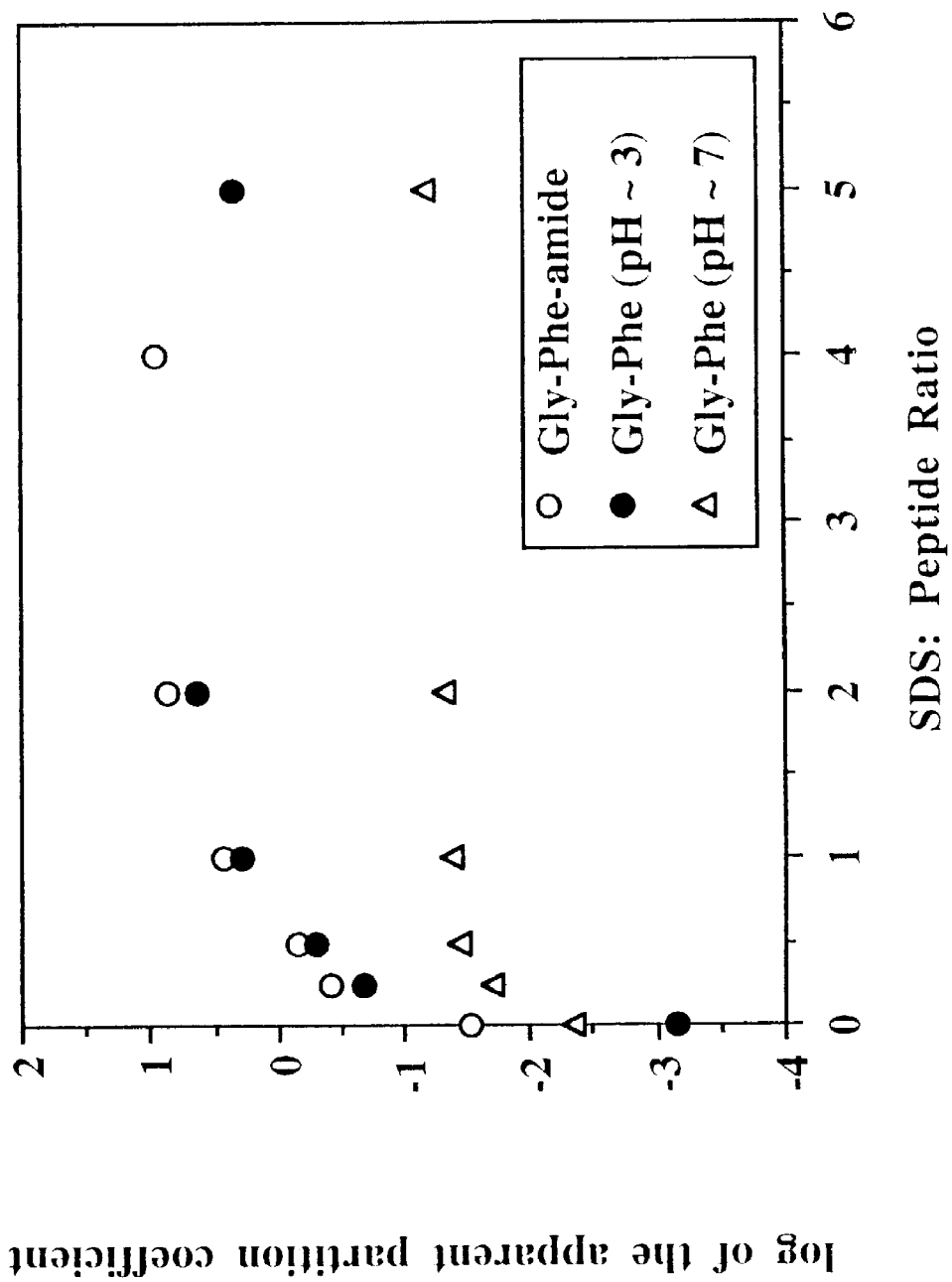
FIG. 1 shows the log of the apparent partition coefficient for the dipeptide Gly-Phe-$NH_2$.

In one aspect, the present invention permits a pharmaceutical substance to be solubilized in an organic solvent by associating the pharmaceutical substance with an amphiphilic material. The pharmaceutical substance is substantially not directly soluble in the organic solvent, but becomes soluble in association with the amphiphilic material. It should be appreciated that by substantially not soluble it is not meant that the pharmaceutical substance is utterly insoluble in an organic solvent. Rather, it is meant that the direct solubility of the pharmaceutical substance in the organic solvent is limited and that it would be desirable to dissolve an amount of the pharmaceutical substance over and above that amount which is directly soluble. That desired additional amount is not soluble in the organic solvent. This is often the case for a pharmaceutical substance which is only slightly soluble in an organic solvent, when it may be desirable to dissolve more of the pharmaceutical substance into the organic solvent then is possible by direct dissolution. According to the present invention, when the pharmaceutical substance is combined with the amphiphilic material, the solubility of the pharmaceutical substance in the organic solvent may be increased by an order of magnitude or more, and is often increased by more than two orders of magnitude relative to direct dissolution of the pharmaceutical substance into the organic solvent, in the absence of the amphiphilic material.

With the present invention, the pharmaceutical substance and the amphiphilic material are in a true, homogeneous solution in the organic solvent. By a true, homogeneous solution, it is meant that the pharmaceutical substance, the amphiphilic material and the organic solvent form a single liquid phase. The present invention is, therefore, distinguishable from the preparation of emulsions, micellar systems and other colloidal suspensions which comprise at least two distinct phases, with one phase being dispersed within the other phase.

To assist in the understanding of the present invention, but not to be bound by theory, it is believed that the pharmaceutical substance and the amphiphilic material are associated in the form of a complex between the amphiphilic material and the pharmaceutical substance, with the complex being substantially not soluble in aqueous liquids at a physiological pH. Preferably, the amphiphilic material and the pharmaceutical substance have oppositely charged ionic portions which associate to form an ion pair complex. Such an ion pair complex is referred to as a hydrophobic ion pair (HIP) complex. Preferably, the pharmaceutical substance comprises a cationic portion which associates with an anionic portion of the amphiphilic material.

The pharmaceutical substance may be any substance which may be administered to a human or animal host for a medical purpose, which is normally a curative or therapeutic purpose. The pharmaceutical substance is preferably directly soluble to some meaningful degree in an aqueous liquid at a physiological pH. As used herein, a physiological pH is a pH of from about 1 to about 8. Preferably, the pharmaceutical substance exhibits a charged character when dissolved in an aqueous liquid at a physiological pH and more preferably exhibits a positively charged, or cationic, character. As used herein, a pharmaceutical substance includes various salt forms of a substance as well as ionic forms and dissociation products, such as may be found in an aqueous solution.

The pharmaceutical substance may comprise a protein or other polypeptide, an analgesic or another material. The following is a non-limiting list of representative types of pharmaceutical substances which may be used with the present invention, with a few specific examples listed for each type of pharmaceutical substance: cholinergic agonists (pilocarpine, metoclapramide); anticholinesterase agents (neostigmine, physostigmine); antimuscarinic drugs (atropine, scopalamine); antidrenergics (tolazoline, phentolamine, propranolol, atenolol); ganglionic stimulating agents (nicotine, trimethaphan); neuromuscular blocking agents (gallamine, succinylcholine); local anesthetics (procaine, lidocaine, cocaine); benzodiazepines (triazolam); antipsychotics (chlorpromazine, triflupromazine, imipramine, amitriptyline, phenelzine); antiparkinson's drugs (L-dopa, dopamine); opioids (morphine, naloxone, naltrexone, methadone); CNS stimulants (theophylline, strychnine); autocoids (histamine, betazole, chlorpheniramine, cimetedine); anti-inflammatories (tolmetin, piroxicam); anti-hypertensives (clonidine, hydralazine, minoxidil); diuretics (metalozone, bumetamide); polypeptides (lysopressin, vasopressin, oxytocin, insulin, calcitonin, gene-related peptide, LHRH agonists, ACTH, growth hormone); antifungals (clotrimazole, miconazole); antimalarials (chloroquine, primaquine); antiprotozoals (pentamidine, melarsoprol); antihelminthics (piperazine, oxamniquine); antimicrobials (streptomycin, erythromycin, cefaclor, ceftriaxone, oxytetracycline, rifampicin, isoniazid, dapsone); aminoglycosides (gentamycin, neomycin, streptomycin); antineoplastics (mechlorethamine, melphalan, doxorubicin, cisplatin); and anticoagulants (heparin). Additionally, the pharmaceutical substance may be a sympathomimetic drug such as catecholamines (epinephrine, norepinephrine); noncatecholamines (amphetamine, phenylephrine); and $\beta_2$-adrenergics (terbutaline, albuterol).

Particularly useful with the present invention are macromolecules such as those of polymers or polypeptides. One advantage of the present invention is that the pharmaceutical substance, when in solution with the amphiphilic material in the organic solvent, retains a substantially native conformation. This is particularly important for materials such as proteins and other polypeptides which are highly susceptible to loss of activity due to unfolding of the molecule from its native conformational structure.

The amphiphilic material may be any material with a hydrophobic portion and a hydrophilic portion. These materials are typically surfactants. The hydrophilic portion is preferably ionic, and more preferably anionic. The hydrophobic portion may be any hydrophobic group such as an alkyl, aryl or alkylaryl group. The hydrophobic portion is preferably a long chain alkyl or substituted alkyl. The amphiphilic material associates with the pharmaceutical substance to form a hydrophobic ion pair which is soluble in the organic solvent when the pharmaceutical substance itself is substantially not soluble in the organic solvent. As used herein, amphiphilic material includes different salt forms of a material as well as ionic forms and dissociation products of a material, such as may be present in a solution.

Examples of anionic amphiphilic materials include sulfates, sulfonates, phosphates (including phospholipids), carboxylates, and sulfosuccinates. Some specific anionic amphiphilic materials useful with the present invention include: sodium dodecyl sulfate (SDS), bis-(2-ethylhexyl) sodium sulfosuccinate (AOT), cholesterol sulfate and sodium laurate. Examples of cationic amphiphilic materials include those having an ammonium group or a guadinium group, including substituted variations of those groups. Specific cationic amphiphilic materials include cetyltrimethylammonium bromide and cetyltrimethylammonium chloride. Preferred amphiphilic materials are those posing little or substantially no toxicological problem for the human or animal host. Particularly preferred anionic amphiphilic materials are SDS and AOT.

The solution of the pharmaceutical substance and the amphiphilic material in the organic solvent may be prepared in any suitable manner. In one embodiment of the present invention, small amounts of the amphiphilic material may be added to an aqueous solution, in which the pharmaceutical substance is initially dissolved, until a precipitate forms of an HIP complex of the pharmaceutical substance and the amphiphilic material. The precipitate may then be recovered and dissolved into an organic solvent to provide the desired solution. For some situations, it may be possible to dissolve the pharmaceutical substance in an aqueous liquid and to dissolve the amphiphilic material in an organic solvent. The aqueous liquid and the organic solvent may then be contacted to effect a partitioning of the pharmaceutical substance into the organic solvent to form an HIP complex with the amphiphilic material. In other situations, it may be possible to dissolve both the pharmaceutical substance and the amphiphilic material into an aqueous liquid. The aqueous liquid may then be contacted with an organic solvent to partition into the organic solvent at least some of the pharmaceutical substance and the amphiphilic material in the form of an HIP complex.

The organic solvent may be any organic liquid in which the pharmaceutical substance and the amphiphilic material, together, are soluble, such as in the form of an HIP complex. The following is a non-limiting, representative list of some organic solvents, with specific exemplary solvents listed in parentheses, which may be used with the present invention: monohydric alcohols (methanol, ethanol, 1-propanol, 2-propanol, 1-butanol, 1-hexanol, 1-octanol, trifluoroethanol); polyhydric alcohols (propylene glycol, PEG 400, 1,3-propanediol); ethers (tetrahydrofuran (THF), diethyl ether, diglyme); alkanes (decalin, isooctane, mineral oil): aromatics (benzene, toluene, chlorobenzene, pyridine); amides (n-methyl pyrrolidone (NMP), N,N-dimethylformamide (DMF)); esters (ethyl acetate, methyl acetate); chlorocarbons ($CH_2Cl_2$, $CHCl_3$, $CCl_4$, 1,2-dichloroethane); and others such as nitromethane, acetone, ethylene diamine, acetonitrile, and trimethyl phosphate.

In one embodiment, the present invention involves the use of amphiphilic materials as ion pairing agents to modulate the solubility and partitioning behavior of pharmaceutical substances such as polypeptides, proteins and basic drugs. Complexes are formed by stoichiometric interaction of an amphiphilic material, such as a detergent or other surfactant (e.g., alkyl sulfate, such as sodium dodecyl sulfate (SDS)), with the basic functional groups of a polypeptide, protein, or organic molecule that are accessible for ion pairing. The basic group may be an amine (as found in the lysine amino acid residue or the N-terminal amino group of a polypeptide) or a guanidinium group (as in arginine). An ion pair is subsequently formed, referred to as a hydrophobic ion pair (HIP) complex. The HIP complex formed will have reduced aqueous solubility, but enhanced solubility in organic solvents.

It has been discovered that an HIP complex may be dissolved in a relatively mild, non-polar organic solvent to form a true homogeneous solution. Included in the present invention is the discovery that the native tertiary structure of the protein is retained even when dissolved in organic solvents such as 1-octanol. The method of the present invention for forming a true homogeneous solution is fundamentally different from any other method for placing proteins into organic solvents, such as those which use suspensions, micelles, microemulsions, or chemical modifications of the protein. This discovery holds important implications in the area of drug delivery and release, including delivery to the body by inhalation and dispersion in a hydrophobic biodegradable matrix. While the decreased aqueous solubility of the HIP complex has been observed previously, the use of an HIP complex precipitate for improved drug delivery is novel. Measurement of the apparent partition coefficient, defined as the ratio of the equilibrium concentration in an organic phase to that in an aqueous phase, demonstrates that the solubility of a peptide or protein in an HIP complex in the organic phase is greater by 2–4 orders of magnitude relative to the chloride salt of the peptide or protein.

Included in the present invention is the discovery that the precipitation of the HIP complex out of aqueous solution may be controlled for the production of uniform HIP complex particles of a desired size. These particles may then form a suspension of the protein. This invention also includes a method of obtaining protein HIP complex particles of specific sizes by controlling the conditions of HIP complex precipitation.

The discovery that HIP complex precipitation can be controlled so as to yield particles of specific size can be exploited to effect the rate of drug released from suspensions. In one embodiment of a method of the present invention, the size of HIP complexes is controlled by controlling the rates of the mixing of a protein solution and the addition of an anionic detergent to the protein solution. The HIP complex can produce very fine suspensions which have limited solubility in water, and the technology can be used to produce particles of varying specific size. The particle size of the HIP complex which is formed in water will depend on the degree of agitation of the protein solution and the rate of counterion addition. The smallest particles are produced with high shear being applied to the aqueous protein solution and slow addition of SDS. This approach is also important in pulmonary drug delivery, where the particle size is critical to delivery to certain sites within the lung. To obtain particles which will be capable of depositing in the pulmonary region upon inhalation, a high speed homogenizer can be used to stir the protein solution and SDS is added dropwise to the agitated solution. Particles in the 2–10 micron range can be obtained using this procedure. Particles of this size are required to get a sufficient amount of protein delivered to the lung to have a beneficial effect. The particles once formed can be separated by centrifugation or filtration. Larger particles will be formed with slow agitation speeds and more rapid addition of SDS. One example of a protein which could benefit from formation into a fine suspension of HIP complex is DNase, an enzyme currently being used by cystic fibrosis patients to dissolve viscous fluid build up in the lung. Other examples include protein and peptide enzyme inhibitors currently being tested for the treatment of emphysema.

The present invention includes a method of controlling the release of a protein from a suspension by controlling the size of the HIP complex particle. The release rate of protein into an aqueous solution from an HIP complex will be much slower than that of the protein itself. This rate will be a function of the particle size of the complex and the solubility of the complex in water or biological fluid. The solubility is a function of the amphiphilic material used and the strength of its association with the protein. Therefore, extended (controlled) release of the protein from the suspension can be achieved. This property permits proteins to be formulated as a suspension for depot injection.

This invention also includes the discovery that uncomplexed protein released from the HIP complex can be extracted back into aqueous medium with retention of its native structure. The native uncomplexed protein can be reclaimed by dissolution in an aqueous solution which contains an excess of chloride or other counterion, indicating that the complexation is an entirely reversible process. The inventors have discovered that the protein of the HIP complex subsequently extracted back into an aqueous medium retains its native structure. This makes HIP methodology useful in the delivery of proteins for use as therapeutic agents.

An important and unique aspect of the present invention is the discovery that HIP complexes display greatly enhanced thermal stability relative to the native protein, both with respect to chemical degradation and denaturation. This suggests that the HIP complex is useful for long term storage of the protein. Further, this aspect of the invention permits high temperature (steam) sterilization of proteins without the loss of biological activity, which until now, could not be accomplished. Currently, polymer delivery systems for proteins are usually sterilized by radiation as proteins are destroyed by heat. The present invention discloses a method by which proteins may be processed by heating at sterilizing temperatures. Further, the enhanced thermal stability of the present invention may be important for the formulation of proteins in maintaining an active enzyme in an organic solvent, and for long term storage of sensitive proteins.

Included in this invention is a method of uniformly distributing a drug throughout a hydrophobic polymer comprising adding a sufficient amount of an anionic detergent to an organic molecule to form a precipitate, isolating the precipitate, and co-dissolving the precipitate and a hydrophobic polymer in an organic solvent to form a homogeneous distribution of the organic molecule within the polymer.

Many of the current systems for the controlled release of proteins make use of biodegradable polymers. There are at least two major problems with such systems. Under the prior art, a protein can only be suspended during the incorporation process, and because of its polar surface does not suspend well. The term "suspension" refers to the dispersion of a substance or substances in another where the boundaries between them are well defined. A material is dispersed in a solvent where the material has limited solubility in that solvent. This leads to an uneven distribution of the drug and irreproducible drug release profiles. Secondly, the water-soluble drug is leached out of the polymer by biological fluids (rather than its controlled release as the polymer is slowly degraded).

The present invention provides a new method for distributing a drug uniformly through a hydrophobic polymer. HIP complex formation permits both proteins and hydrophobic polymers to possess similar solubility parameters, thus facilitating incorporation of the protein into the polymer matrix. The present inventors have discovered that HIP complexes may be uniformly distributed in biodegradable polymers as they possess a solubility in solvents that will also dissolve the polymer. Where the HIP complex does not dissolve in the solvent used it will suspend easily as a result of its hydrophobic surface.

The present invention wherein the drugs being delivered are included in the polymer matrix in an HIP complex represents three advantages over the biodegradable polymer systems: (1) the hydrophobic polymers can be better mixed with the drug in its lipophilic ion-pair state; (2) the drug forms hydrophobic particles within the polymer, and avoids the problem of the formation of a concentration of polar particles at the interface of the polymer leading to the "burst" effect; (3) the hydrophobic particles dispersed within the biodegradable polymer are not leached out by biological fluids which result in a predictable release rate. The inventors have discovered the use of the HIP complex to control (retard or extend) the release of a drug at a predictable rate, resulting in part from a more uniform formulation.

One embodiment of this invention includes a method for achieving a true homogeneous solution of biologically active proteins and polypeptides in a organic solvent. None of the methods by which enzymatic activity is achieved in a non-aqueous environment achieve a true protein solution. The present inventors have discovered that the HIP complex can be redissolved in an organic solvent such that a true homogeneous solution is formed. This discovery has important ramifications for controlling the enzymatic activity of proteins in the body. Through the formation of HIP complexes, enzymes and other proteins can be solubilized in a variety of organic solvents, including ethanol, propylene glycol and glycols in general, N-methyl pyrrolidone (NMP) and others. These materials should have altered enzymatic activity and specificity. It is important to note that use of HIP to form true solutions of biologically active proteins and polypeptides is a fundamentally different approach from any previously described for achieving enzymatic activity in non-aqueous media.

Also included in this invention is the discovery that the HIP complex dissolved in organic solvent can be extracted back into aqueous medium with retention of the native protein structure. This discovery has potential use in the purification of proteins. A protein having a pH different from others in a mixture may be extracted or preferentially precipitated from the mixture via HIP complex formation.

The present invention further includes a method of obtaining a stabilized protein comprising precipitating a protein in the HIP complex. Much research effort has been directed into developing stabilized lyophilized formulations of proteins, including by the addition of cryoprotectants. The HIP complex may, in many cases, provide a simple alternative to obtaining a stabilized protein. A protein in the solid HIP complex has enhanced stability and resistance to degradation through storage, shipping, and handling. Chemical stability is conferred because the amount of water present is relatively low, as in lyophilized powders. To reconstitute the protein, the HIP complex is suspended in a diluent containing a significant chloride concentration (e.g., phosphate buffered saline (PBS) or normal saline). Most HIP complexes redissolve rapidly and completely, leaving a solution whose only additive is a small amount of SDS. The protein can also be stored as a stable entity by dissolving or suspending the HIP complex in an organic solvent or solvent mixture. To form an aqueous solution of the protein, the solution or suspension can be shaken with water containing chloride. In cases where the organic solvent is immiscible with water, the protein will partition into the water.

An additional embodiment of this invention is a method of incorporating proteins into lipid vesicles, liposomes, or detergent micelles. Shaking of an oil-water mixture with an HIP complex of a protein leads to emulsification, indicating that a HIP complex can more easily be introduced into emulsion delivery systems than the protein alone. Systems for such use can be designed using either the insoluble material in suspension formulations or in oil formulation, such as oil in water emulsions, other examples include nasal and pulmonary aerosols, ophthalmic suspensions, transdermal patches, lozenges, chewing gum, buccal and sublingual systems, and suppositories.

Another aspect of this invention is the reduction of the bitter taste of drugs incorporated into HIP complexes, since only compounds in solution are tasted. Therefore, this invention includes a method for improving the taste of orally administered drugs by formation of insoluble HIP complexes with such drugs. The taste of a substance is detected by receptors in the tongue. A major approach to modifying the taste of a drug is to alter its solubility in saliva. If the solubility is sufficiently low the taste will not be noted. The low solubility of the HIP complex in biological fluids, including saliva, can be used to mask the flavor of a drug. Another way to mask taste is to partition the drug into an oil, such as olive oil. This can then be given as an oil in water emulsion with flavoring agents added to the outer water phase. HIP complex formation would provide the drug with the necessary high oil to water partition coefficient.

The term "hydrophobic ion-pairing (HIP)" as used in this disclosure refers to the interaction between an amphiphilic material and a pharmaceutical substance. Preferred amphiphilic materials include anionic detergents containing long chain alkyl groups, such as SDS, which interact with proteins and other polypeptides. "HIP complex derivatives" are substances modified by formation of a hydrophobic ion-pair. The anionic detergent interacts with an oppositely charged polypeptide. This interaction has been termed HIP because it appears to be primarily electrostatic in nature.

As used in the present invention, the term "anionic detergents" encompasses any hydrophobic material that is a salt of an acid which can be employed to modify solubility properties in the described way, including sulfates, sulfonates, phosphates, and carboxylates. Sulfates are the salts of the stronger acids in this series and, therefore, the most efficient at forming ion pairs. Provided that the alkyl chains or aryl rings are of 8–18 carbons in length, they are potential candidates for HIP methodology. Presumably cationic detergents, such as dodecylamine hydrochloride or cetyltrimethylammonium bromide (CTAB), may also work for negatively charged polypeptides.

Although the solution having the HIP complex dissolved in the organic solvent is itself a valuable product the solution may also be used in the preparation of additional pharmaceutical products. In particular the solution may be used to prepare a powder of solid particles comprising the pharmaceutical substance and the amphiphilic material. In a preferred embodiment, the solution is subjected to antisolvent precipitation processing to prepare a powder of solid particles. Powders may be prepared having particles of an ultrafine size and a relatively narrow size distribution. Also, hollow elongated, fiber-like particles of a small size may be prepared. These particles have unique properties which may be desirable for various pharmaceutical applications.

Figure 12:
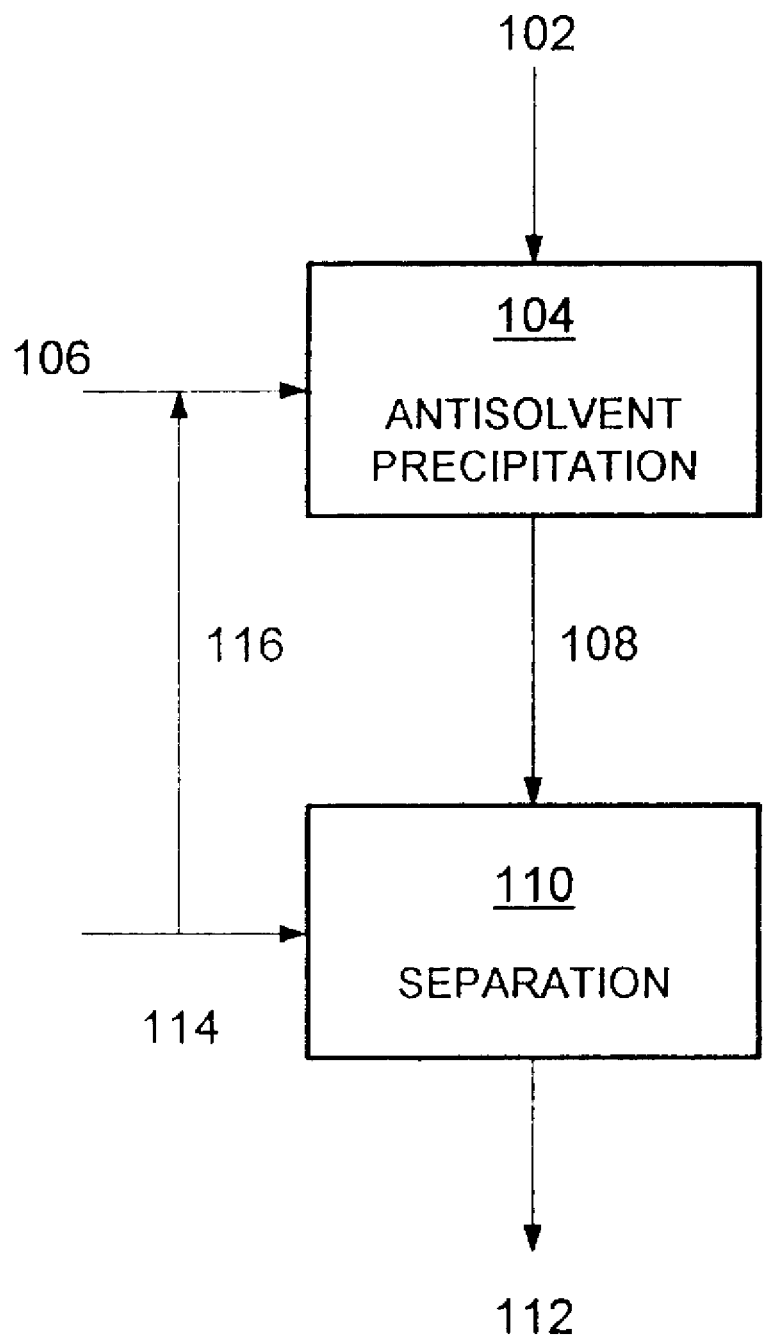
FIG. 12 shows a process flow diagram for one embodiment of an antisolvent precipitation method for producing pharmaceutical powders.

With reference to FIG. 12, one embodiment of an antisolvent precipitation method of the present invention is shown. A liquid feed solution 102 is provided having a pharmaceutical substance and an amphiphilic material dissolved together in an organic solvent, which is used as a carrier liquid for processing of the pharmaceutical substance. The liquid feed solution 102 is subjected to antisolvent precipitation 104 in which the liquid feed solution 102 is contacted with an antisolvent fluid 106. During the antisolvent precipitation 104, the antisolvent fluid 106 invades the organic solvent of the liquid feed solution 102, resulting in precipitation of solid particles comprising the pharmaceutical substance and the amphiphilic material. The resulting mixture 108, having the precipitated particles, is subjected to separation 110 in which solid particles 112 are separated from the exiting fluid 114. A portion 116 of the exiting fluid 114 is recycled to form a part of the antisolvent fluid 106 and a portion 118 of the exiting fluid 114 is bled from the system to prevent an undesirable build-up of the organic solvent in the system. Continuous or batch processes other than the process shown in FIG. 12 may also be used according to the present invention.

The antisolvent fluid is a fluid in which the pharmaceutical substance and the amphiphilic material, in association, are substantially not soluble. It should be understood that it is possible that the antisolvent fluid may be capable of dissolving some amount of the pharmaceutical substance and the amphiphilic material without departing from the scope of the present invention. The antisolvent fluid, however, is substantially incapable of dissolving a significant portion of the pharmaceutical substance and the amphiphilic material from the liquid feed solution such that at least a significant portion of pharmaceutical substance and the amphiphilic material are, in effect, not soluble in the antisolvent fluid. Also, the antisolvent fluid is at least partially miscible with the organic solvent such that the antisolvent fluid is capable of penetrating into the organic solvent sufficiently to cause the desired precipitation of the pharmaceutical substance and the amphiphilic material.

Preferably, the antisolvent fluid 106 is a gas and the antisolvent precipitation 104 is conducted under thermodynamic conditions which are near critical or supercritical relative to the antisolvent fluid. Preferably, the antisolvent precipitation is such that the antisolvent fluid is at a reduced pressure of greater than 0.5, with the reduced pressure being the ratio of the total pressure during the antisolvent precipitation 104 to the critical pressure of the gaseous antisolvent fluid 106. More preferably, the contacting occurs at a reduced pressure of from about 0.8 to about 1.2 relative to the antisolvent fluid.

The antisolvent fluid may comprise any suitable fluid for near critical or supercritical processing. These fluids include carbon dioxide, ammonia, nitrous oxide, methane, ethane, ethylene, propane, butane, pentane, benzene, methanol, ethanol, isopropanol, isobutanol, fluorocarbons (including chlorotrifluoromethane, monofluoromethane, hexafluoraethane and 1,1-difluoroethylene), toluene, pyridine, cyclohexane, m-cresol, decalin, cyclohexanol, o-xylene, tetralin, anilin, acetylene, chlorotrifluorosilane, xenon, sulfur hexafluoride, propane, and others. Carbon dioxide, ethane, propane, butane and ammonia are preferred antisolvent fluids.

For many pharmaceutical substances, it is desirable to use an antisolvent fluid which permits processing at relatively mild temperatures. This is particularly important for processing proteins and other polypeptides which are susceptible to a loss of biological activity when subjected either to very low temperatures or to very high temperatures. For applications involving proteins and other large polypeptides, the antisolvent fluid should preferably have a critical temperature of from about 0° C. to about 50° C. Included in this category of antisolvent fluids are carbon dioxide, nitrous oxide, ethane, ethylene, chlorotrifluoromethane, monofluoromethane, acetylene, 1,1-difluoroethylene, hexafluoroethane, chlorotrifluorosilane, and xenon. A particularly preferred antisolvent fluid is carbon dioxide because it is readily available, non-toxic, and has a critical temperature of 31° C. and a critical pressure of 72.9 atm, which permits processing under relatively mild conditions.

The contacting of the liquid feed solution 102 with the antisolvent fluid 106 during the antisolvent precipitation 104 may be accomplished using any suitable contacting technique and contacting apparatus. Preferably, the liquid feed solution 102 is sprayed as small droplets into the antisolvent fluid 106. A sonicated spray nozzle, which is vibrated ultrasonically, has been found to work well because it is capable of producing very small droplets of a relatively uniform size and is, therefore, conducive to preparation of ultrafine powders having particles of a narrow size distribution. The contacting may be performed in a batch operation or continuously. Also, continuous operation could involve contacting by concurrent flow or countercurrent flow.

The separation 110 may be accomplished using any suitable separation technique and apparatus. For example, the separation may involve simple density separation, filtration or use of a centrifuge.

The antisolvent precipitation process of the present invention may be used to produce ultrafine particles of a narrow size distribution and which are often of spheroidal shape. These ultrafine particles may be as large as about 10 microns or may be 1 micron or smaller. The size of the particles produced will depend upon the particular pharmaceutical substance and the processing conditions used.

In general, particle size becomes larger as the viscosity and surface tension of the organic solvent increases. For example, the use of ethanol as an organic solvent would generally produce smaller particles than the use of isopropanol as an organic solvent. Also, particles generally tend to become larger in the vicinity of the critical temperature as the process temperature approaches the critical temperature from above. If the process temperature is too high, however, then particle sizes generally tend to become larger again. For example, using carbon dioxide, the smallest particles seem to be produced around a temperature of about 35° C., with larger particles generally being produced at substantially higher and lower temperatures. When using carbon dioxide, the pressure is preferably within the range of from about 70 bars to about 90 bars.

It has been found that the method of the present invention may be used to produce particles of a narrow size distribution. Preferably, particles produced in the gas antisolvent precipitation method of the present invention are such that greater than about 90 weight percent of the particles are within about 50 percent larger or smaller than a weight average particle size.

In addition to varying the size of the particles, it is also possible to vary the shape of the particles produced. For example, it is possible to produce spheroidal shaped particles which have good flowability properties. Also, it has been found that hollow fiber-like particles may be made according to the present invention, the length of which may vary depending upon processing conditions. These fiber-like particles have a tubular quality in that they comprise an elongated body, of a substantially rounded cross-section, which has a hollow interior, which typically is open at least one end of the elongated body, and is preferably open at both ends of the elongated body.

It has been found that these fiber-like particles tend to form when the pharmaceutical substance is subjected to gas antisolvent precipitation at a very high concentration in the organic solvent, such that the molecules of the pharmaceutical substance tend to be entangled when dissolved in the organic solvent. Macromolecules are particularly susceptible to such entanglement in solution and are, therefore, preferred for making these fiber-like particles. Such macromolecules include polymers and polypeptides, including proteins. The concentrations required for any particular pharmaceutical substance will depend upon the specific pharmaceutical substance being processed, but concentrations of 5 to 10 weight percent or higher, relative to the organic solvent, may be required for many polypeptide macromolecules.

The fiber-like particles typically have a diameter of smaller than about 100 microns, preferably smaller than about 50 microns. In some cases, the diameter may be as small as 10 microns or less. Length may vary from about 0.3 mm or less to as long as 1 cm or more, and is preferably longer than about 0.5 mm and more preferably longer than about 1 mm. Generally, a lower flow rate of the liquid feed solution during gas antisolvent precipitation tends to produce longer fiber-like particles and a higher flow rate tends to produce shorter fiber-like particles.

These hollow, fiber-like particles offer a number of advantages for use in the pharmaceutical industry. One advantage is that these fiber-like particles have a shape that will not, upon ingestion, pass as easily as a spheroidal particle through the stomach. The fiber-like particles should, therefore, tend to have a longer retention time in the stomach region and would, accordingly, be available in a stomach region for a longer period of time for the desired pharmaceutical treatment. Another advantage of the fiber-like particles is that, because they are hollow, it is possible to place smaller particles of another pharmaceutical substance inside the hollow interiors. For example, small particles of morphine or pentamidine could be loaded into the hollow interiors of a protein-based fiber-like particle which is protein-based.

In addition to the pharmaceutical substance and the amphiphilic material, a biodegradable polymer may also be incorporated into the solid particles of the present invention, as noted previously, for controlled release of the pharmaceutical substance. A biodegradable polymer may be incorporated in the antisolvent precipitation method of the present invention by co-dissolving the biodegradable polymer in the organic solvent along with the pharmaceutical substance and the amphiphilic material. The particles produced during antisolvent precipitation will then contain the biodegradable polymer as well as the amphiphilic material and the pharmaceutical substance. The biodegradable polymer may be used in any convenient amount relative to the pharmaceutical substance. The weight ratio of the biodegradable polymer to the pharmaceutical substance could vary from about 0.1 to 1 to about 100,000 to 1 depending upon the application. Most controlled release applications, however, will involve a ratio of from about 10 to 1 to about 100 to 1.

Incorporation of the biodegradable polymer into the solid particles may be used to delay release of the pharmaceutical substance and to permit sustained release of the pharmaceutical substance over some extended period of time. It has been found that the release profile from a particle of the present invention in an aqueous buffer solution for the pharmaceutical substance is relatively constant and that a sudden initial release, or "burst effect," is avoided. This indicates that the pharmaceutical substance is not concentrating near the surface of the particle and that the particle comprises an intimate and homogeneous mixture of the pharmaceutical substance, the amphiphilic material and the biodegradable polymer.

Any biodegradable polymer may be used which may be co-dissolved into the organic solvent along with the pharmaceutical substance and the amphiphilic material. Examples of such biodegradable polymers include those having at least some repeating units representative of polymerizing at least one of the following: an alpha-hydroxycarboxylic acid, a cyclic diester of an alpha-hydroxycarboxylic acid, a dioxanone, a lactone, a cyclic carbonate, a cyclic oxalate, an epoxide, a glycol, and anhydrides. Preferred is a biodegradable polymer comprising at least some repeating units representative of polymerizing at least one of lactic acid, glycolic acid, lactide, glycolide, ethylene oxide and ethylene glycol. The biodegradable polymers may be a homopolymer or a copolymer of two or more different monomers. Preferred homopolymers include poly (lactic acid), polylactide, poly(glycolic acid), polyglycolide and poly(ethylene glycol).

A further aspect of the present invention involves use of solid particles of the present invention in pharmaceutical delivery applications. To deliver a pharmaceutical substance, solid particles having the pharmaceutical substance and the amphiphilic material according to the present invention are introduced into a human or animal host.

In one embodiment, the solid particles are inhaled for pulmonary delivery. For pulmonary delivery, it is preferred that greater than about 90 weight percent of all of the solid particles in an administered pharmaceutical formulation are of a size smaller than about 10 microns and more preferably at least about 90 weight percent of said particles are smaller than about 6 microns, and even more preferably at least about 90 weight percent of all of said solid particles are from about 1 micron to about 6 microns. Particularly preferred for pulmonary delivery applications are particles of from about 2 microns to about 5 microns in size. These particles may also comprise a biodegradable polymer for delayed and/or sustained release of the pharmaceutical substance. The ultrafine size and narrow size distribution of the solid particles of the present invention permit a much higher utilization of the pharmaceutical substance for pulmonary delivery than the low utilization experienced with present methods for pulmonary delivery of pharmaceutical substances. Whereas current aerosol and nebulization techniques may use only 10 percent of a pharmaceutical substance which is administered, with the particles of the present invention, 80 percent or more of a pharmaceutical substance which is administered may be utilized.

The solid particles of the present invention may also be placed in a suspension and the suspension injected into the host. For intramuscular or subcutaneous injection, the particles will often comprise a biodegradable polymer for sustained release of the pharmaceutical substance and the particles will typically be from about 10 microns to about 100 microns in size, although smaller or larger particles may be used in some applications.

For intravenous injection, substantially all particles should be of a size smaller than about 1 micron so that the particles will not be susceptible to creating a blockage within the circulatory system. The particles may comprise a biodegradable polymer, if desired.

For any treatment requiring injection of a suspension over a prolonged period, such as for a micropump which continuously injects a suspension at a slow rate, greater than about 90 weight of the particles are preferably smaller than about 1 micron to reduce problems associated with settling of the solid particles. More preferably, substantially all particles are smaller than about 1 micron.

The fiber-like particles should be useful in a number of pharmaceutical applications to deliver a pharmaceutical substance to a location where it is needed. For example, due to their hollow, fibrous shape, these particles should tend to absorb water due to capillary action. The fiber-like particles, may, therefore accelerate biodegradation of a biodegradable polymer relative to a particle which is not hollow. Also, the fiber-like particles could be woven or spun, alone or with other fibrous materials, to incorporate a pharmaceutical substance into a medical product using the woven or spun materials. For example, the fiber-like particles could be made to include a growth factor. Some of the fiber-like particles then may be used in making wound coverings, from which the growth factor could be delivered to the wound. Also, the fiber-like particles could be incorporated into grafts, such as arterial grafts, by spinning with other fibers such as DACRON™ or another material. The fiber-like particles could include a pharmaceutical substance to enhance healing in the vicinity of the graft or the acceptance of the graft. Moreover, the fiber-like particles could be used in the manufacture of patches for delivery of a pharmaceutical substance, including patches for sublingual or buccel delivery of a pharmaceutical substance.

Particles of the present invention, having the ion-paired pharmaceutical substance, may also be used to enhance properties of immune system boosters to elicit an immune system response. Rather than injecting a solution of an antigenic protein or other peptide with an adjunct, such as aluminum hydroxide, to cause precipitation after injection, a suspension of the ion-paired particles of the present invention could be used. In another embodiment, the particles of the present invention could be used in cements, to deliver a growth factor to help heal broken bones or teeth.

The invention will now be described with reference to the following non-limiting examples.

EXAMPLES

The methods used for measuring apparent partitioning coefficients are described in Example 1. The measurement of the behavior of the Gly-Phe-NH$_2$:SDS complex is described in Example 2. The behavior of the 8-Arg-vasopressin:SDS complex, leuprolide:SDS complex, neurotensin:SDS complex, and bradykinin:SDS complex are described in Example 3. The behavior of the insulin:SDS complex is described in Example 4. The dissolution of the insulin:SDS complex as a function of the organic solvent is described in Example 5. Further behavior of the leuprolide:SDS complex is described in Example 6. Example 7 describes the CD spectrum of the insulin:SDS complex. Example 8 describes the thermal stability of the insulin:SDS complex. Example 9 describes the behavior of other large proteins with SDS, specifically, human growth hormone. The behavior of bovine pancreatic trypsin inhibitor with SDS is described in Example 10, and Example 11 describes the behavior of human serum albumin with SDS. The melting point of the SDS:insulin HIP complex was studied (Example 12).

Example 13 describes a method for forming a fine HIP complex suspension suitable for pulmonary delivery. Example 14 describes a method for achieving uniform distribution of a protein throughout a hydrophobic polymer suitable for use as an injectable implant. Example 15 describes the use of the HIP complex for improved storage of proteins. The use of protein precipitation in the HIP complex for protein purification is described in Example 16. A method of administering a protein dissolved as an HIP complex in organic solvent is described in Example 17. Example 18 describes the preparation of a drug with reduced bitter taste.

Examples 19–29 demonstrate batch preparation of particles using gas antisolvent precipitate. Examples 30–32 demonstrate continuous preparation of particles using gas antisolvent precipitation.

Example 1

Measurement of Apparent Partition Coefficients

The relative solubilities in two phases is given in terms of an apparent partition coefficient. The apparent partition coefficient is defined as the ratio of the equilibrium concentration in an organic phase to that in an aqueous phase. The actual value of the apparent partition coefficient, P, is dependent on the two solvent systems employed. In all cases herein described, the organic phase is 1-octanol and the aqueous phase is water alone or with a minimal amount of HCl added.

Apparent partition coefficients were measured by dissolving a peptide in 1.25 ml of an aqueous solution. Before SDS addition, the pH was measured on a Beckman pH meter. Upon addition of an SDS solution, the solutions turned cloudy and a precipitate formed immediately. An equal volume of 1-octanol was added and the mixtures agitated, and then left undisturbed for several hours. Prior to analysis, the tubes were spun for 10 minutes at 4000 g. Each layer was removed and the absorbance measured on a Beckman DU-64 UV-visible spectrophotometer using 1 cm quartz cells. All apparent partition coefficients were corrected for changes in pH with differing SDS concentrations.

Results are described as logarithms of the apparent partition coefficient. A log P value of 0 means that the compound is equally soluble in water and the organic phase. A positive log P value means the peptide is more soluble in the organic phase than in water and a negative log P values indicate a greater aqueous solubility than in the organic solvent. All of the log P values reported herein have been corrected for slight changes in solubility with Ph.

Example 2

Apparent Partitioning Coefficient for Gly-PheNH$_2$

The logarithm of the apparent water/1-octanol partition coefficients for Gly-Phe-NH$_2$ Gly-Phe amid, 0.6 mg/ml, pH about 5) and Gly-Phe (0.6 mg/ml at pH 7 and pH 3) as a function of SDS to peptide ratio are shown in FIG. 1. Apparent partition coefficients were measured as described in Example 1.

In order for HIP to occur, the polypeptide must contain at least one basic group (either a lysine or arginine side chain or a free N-terminal amino group). Gly-Phe-NH$_2$ contains a single basic group, and at pH 7 forms a 1:1 complex with SDS. The complex precipitates from aqueous solution, but readily partitions into 1-octanol, as shown in FIG. 1. For Gly-Phe itself, which exists in a zwitterionic form at neutral pH, a complex with SDS is formed with difficulty, and little enhancement of the partition coefficient is observed. However, by lowering the pH to less than 4, the carboxylate group of Gly-Phe becomes protonated, leaving the molecule with an overall positive charge and again, a hydrophobic ion pair can be formed. Partitioning of Gly-Phe at pH 3 mirrors the marked increase seen for Gly-Phe-NH$_2$. Therefore, even for acidic peptides, lowering the pH may permit hydrophobic ion pair complexes to be formed.

Example 3

Behavior of Protein:SDS Complexes.

Figure 2:
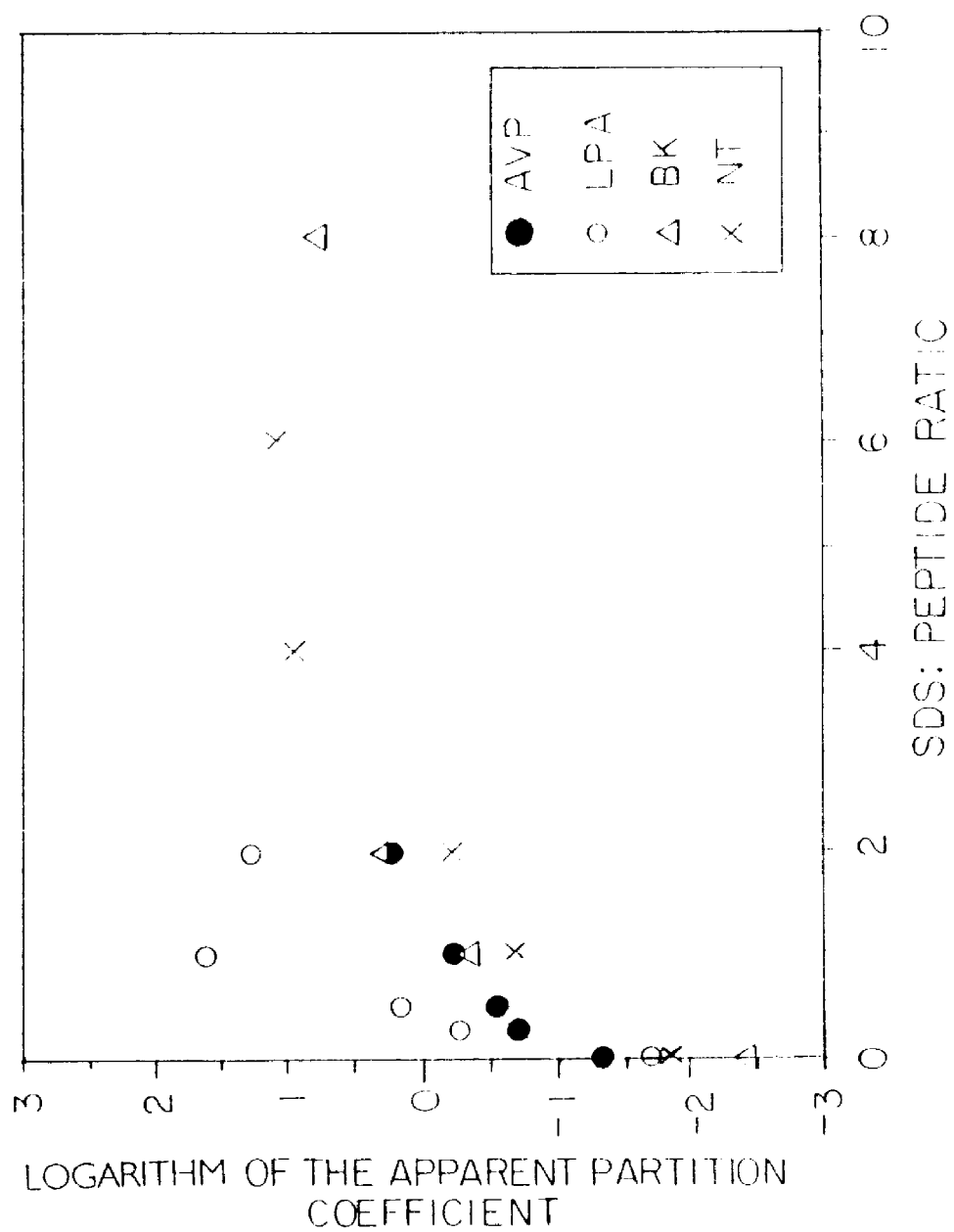
FIG. 2 shows the log of the apparent partition coefficient for 8-Arg-vasopressin (AVP).

The logarithms of the apparent water/1-octanol partition coefficient for AVP (0.49 mg/ml, pH 5), leuprolide (LPA) (0.5 mg/ml, pH 6), neurotensin (NT)(0.y mg/ml, pH x), and bradykinin (BK) (0.y mg/ml, pH x) are shown in FIG. 2. Apparent partition coefficients were measured as described in Example 1.

Peptides larger than Gly-Phe-NH$_2$ can interact with SDS to form HIP-complexes with enhanced solubility in organic solvents. AVP is a nonapeptide hormone which controls water and salt elimination in the body. It contains two basic groups, the N-terminal amino group and the guanidinium side chain of Arg$^8$, and no acidic groups. Stoichiometric addition of SDS produces a precipitate from an aqueous solution (pH 7) which readily partitions into a 1-octanol (FIG. 2). At a mole ratio of 2:1 (SDS:peptide), the solubility in 1-octanol actually exceeds the solubility in water by more than tenfold (i.e., log P>1). Overall, the apparent partition coefficient for AVP was increased by nearly four orders of magnitude.

Example 4

Behavior of Insulin:SDS Complex

Figure 3:
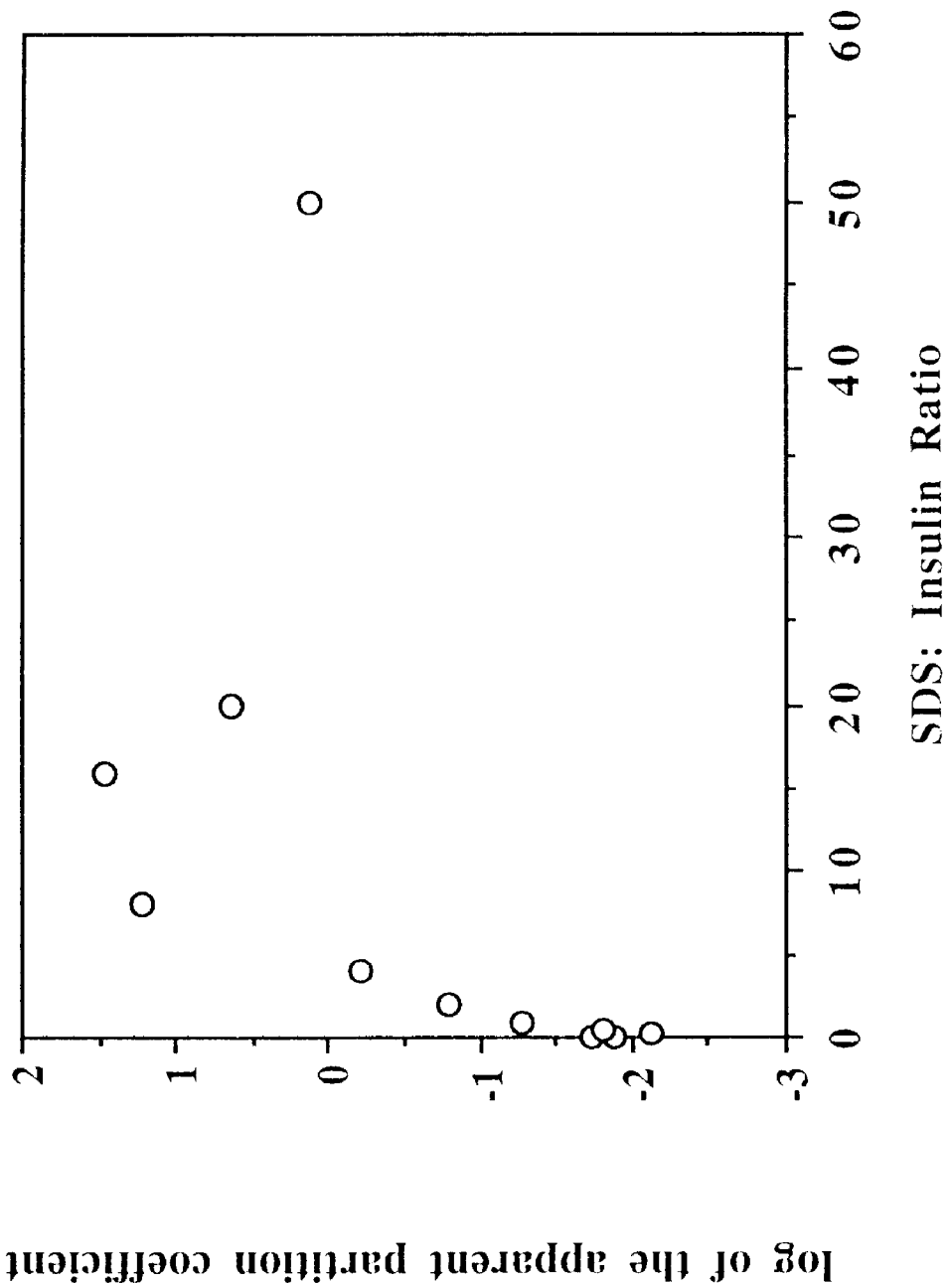
FIG. 3 shows the log of the apparent partition coefficient for insulin.

The logarithm of the apparent partition coefficient of insulin as a function of SDS ratio is shown in FIG. 3.

Polypeptides which contain both acidic and basic groups can also form hydrophobic ion pairs. Insulin contains six basic groups (one Arg, one Lys, two His, and two F-terminal amino groups) and four acidic groups. By lowering the pH to 2.5, all of the acidic groups (which are carboxylic acids) become protonated and the only remaining charges are due to the basic functional groups, producing an overall charge of +6.

The solubility of insulin is altered dramatically upon addition of stoichiometric amounts of SDS (FIG. 3). The solubility of an insulin-SDS complex approaches 1 mg/ml (0.17 mM) in 1-octanol, and its apparent partition coefficient increases by nearly four orders of magnitude. At higher SDS concentrations, the apparent partition coefficient decreases, because the solubility of insulin in water increases again, presumably due to micelle formation.

Example 5

Dissolution of Insulin-SDS Complex as a Function of the Organic Solvent

Dissolution of insulin-SDS complexes in other solvents was investigated as well (Table 1). Precipitates of SDS-insulin complexes were isolated and added to various organic solvents. Some degree of polarity appears to be necessary to obtain measurable solubility in the organic phase, as partitioning into chlorocarbons (CH$_2$Cl$_2$ 1-chlorooctane, and CCl$_4$) and alkanes (mineral oil, hexane) could not be detected using UV-visible absorption spectroscopy. Besides alcohols, SDS-insulin complexes are soluble in N-methylpyrrolidone (NMP), trimethylphosphate (TMP), polyethylene glycol, ethanol, and t-butanol.

TABLE 1

PARTITIONING OF INSULIN INTO NON-AQUEOUS SOLVENTS

| Orgainc Solvent | Log P | Apparent Sol. (mg/ml) |
|---|---|---|
| 1-octanol | $\geq 1.2$ | $\geq 1.0$ |
| CCl$_4$ | not detectable | insoluble |
| Mineral Oil | not detectable | insoluble |
| CH$_2$Cl$_2$ | not detectable | insoluble |
| Dimethoxyethane | not detectable | not determined |
| Hexane | not detectable | insoluble |
| 1-Chlorooctane | not detectable | insoluble |
| THF | miscible | not determined |
| Acetone | miscible | not determined |
| Ether | not detectable | insoluble |
| DMF | not determined | $\geq 1.0$ |
| NMP | miscible | $\geq 1.0$ |
| Ethyl acetate | miscible | insoluble |
| PEG 400 | miscible | $\geq 0.2$ |
| Trimethyl phosphate | miscible | $\geq 0.15$ |
| Ethanol | miscible | $\geq 1.0$ |
| i-Propanol | miscible | $\geq 1.0$ |
| Methanol | miscible | $\geq 1.0$ |
| Propylene Glycol | miscible | $\geq 0.5$ |
| TMP | miscible | $\geq 0.2$ |
| Trifluoroethanol | miscible | $\geq 0.5$ |

Example 6

Behavior of Leuprolide:SDS Complex

Leuprolide acetate is a luteinizing hormone releasing hormone (LHRH) agonist used in the treatment of endometriosis. It contains 9 amino acid residues and two basic functionalities (a histidine and an arginine group). Both termini are blocked. Stoichiometric amounts of SDS were added to an aqueous solution of leuprolide (0 and 0.5 mg/ml, pH 6.0), resulting in formation of a precipitate. The apparent partition coefficient of the SDS-leuprolid complex (FIG. 2) exhibited a log P into 1-octanol greater than 1.0.

Example 7

CD Spectrometry of the SDS-Insulin Complex

Two important considerations for proteins dissolved in non-aqueous solvents are whether native structures are retained and whether the material can be extracted back into an aqueous phase. The secondary composition of a 6:1 SDS-insulin complex dissolved in neat 1-octanol at 5° C. is shown in FIG. 3. The insulin concentration was 61 ug/ml.

CD spectra were recorded on an Aviv 62DS spectrophotometer equipped with a thermoelectric temperature unit. All temperatures were measured ±0.2° C. Samples were placed in strain-free quartz cells (pathlength of 1 mm) and spectra obtained taking data every 0.25 nm using a three second averaging time, and having a spectral bandwidth of 1 nm.

Analysis of the CD spectrum, using an algorithm based on the methods of Johnson (1990) Genetics 7:205–214 and van Stokkum et al. (1990) Anal. Biochem. 191:110–118, indicates that the alpha-helix content of insulin in octanol is 57%, similar to that found for insulin in aqueous solution (57%) (Melberg and Johnson (1990) Genetics 8:280–286) and in the solid state by x-ray crystallography (53%) (Baker et al. (1988) Phil. Trans. R. Soc. London B319, 369–456). The spectra are slightly more intense than those reported for insulin in water (Pocker and Biswas (1980) Biochemistry 19:5043–5049; Melberg and Johnson (1990) supra; Brems et al. (1990) Biochemistry 29:9289–9293). The relative intensity of the 222 nm band to the 208 nm band is similar to that observed for insulin at high concentrations (Pocker and Biswas (1980) supra). This represent the first example of native-like structure in a protein dissolved in a neat organic solvent.

Figure 4:
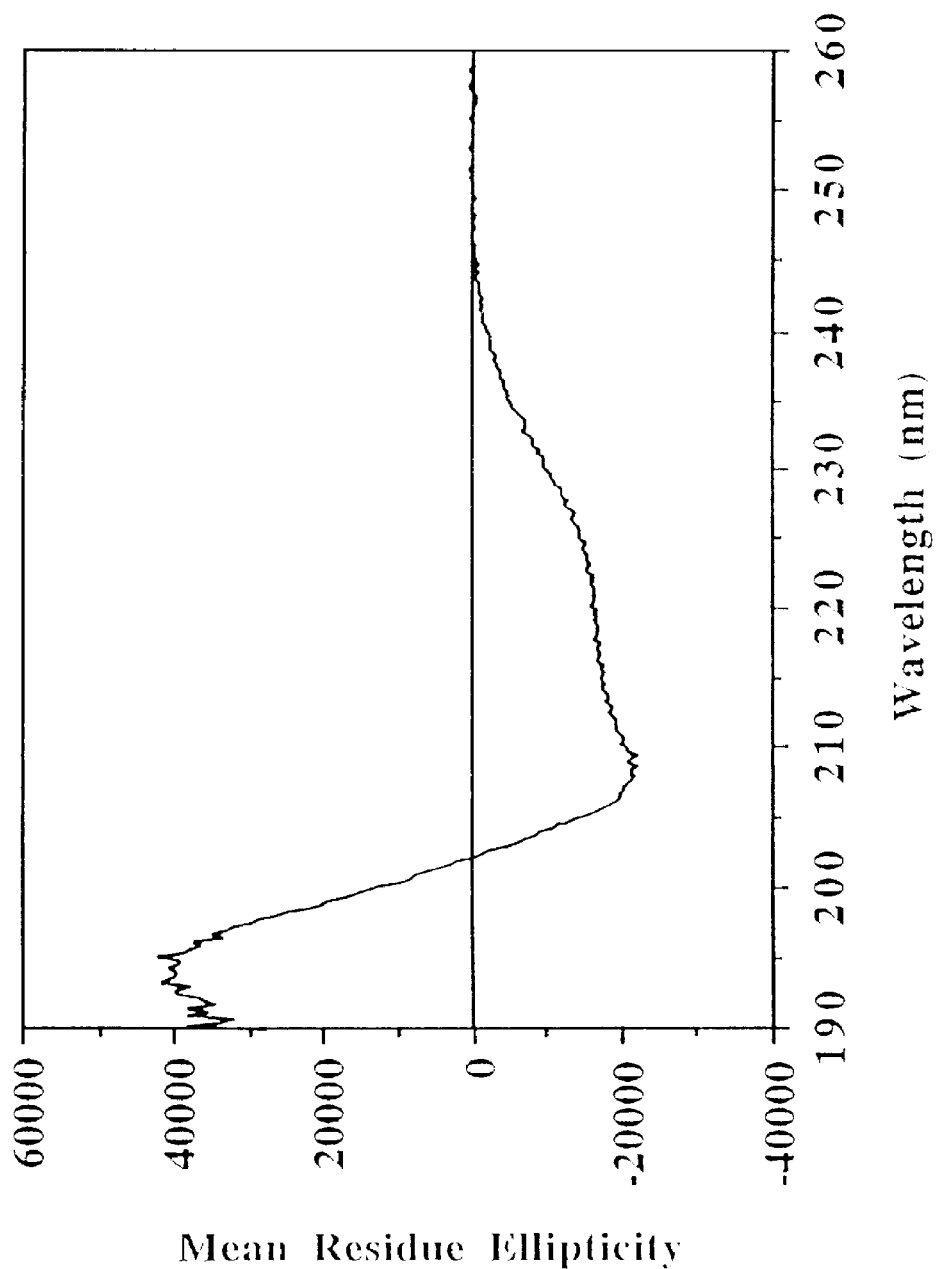
FIG. 4 shows the CD spectra of a 6:1 SDS-insulin complex in 1-octanol.
Figure 5:
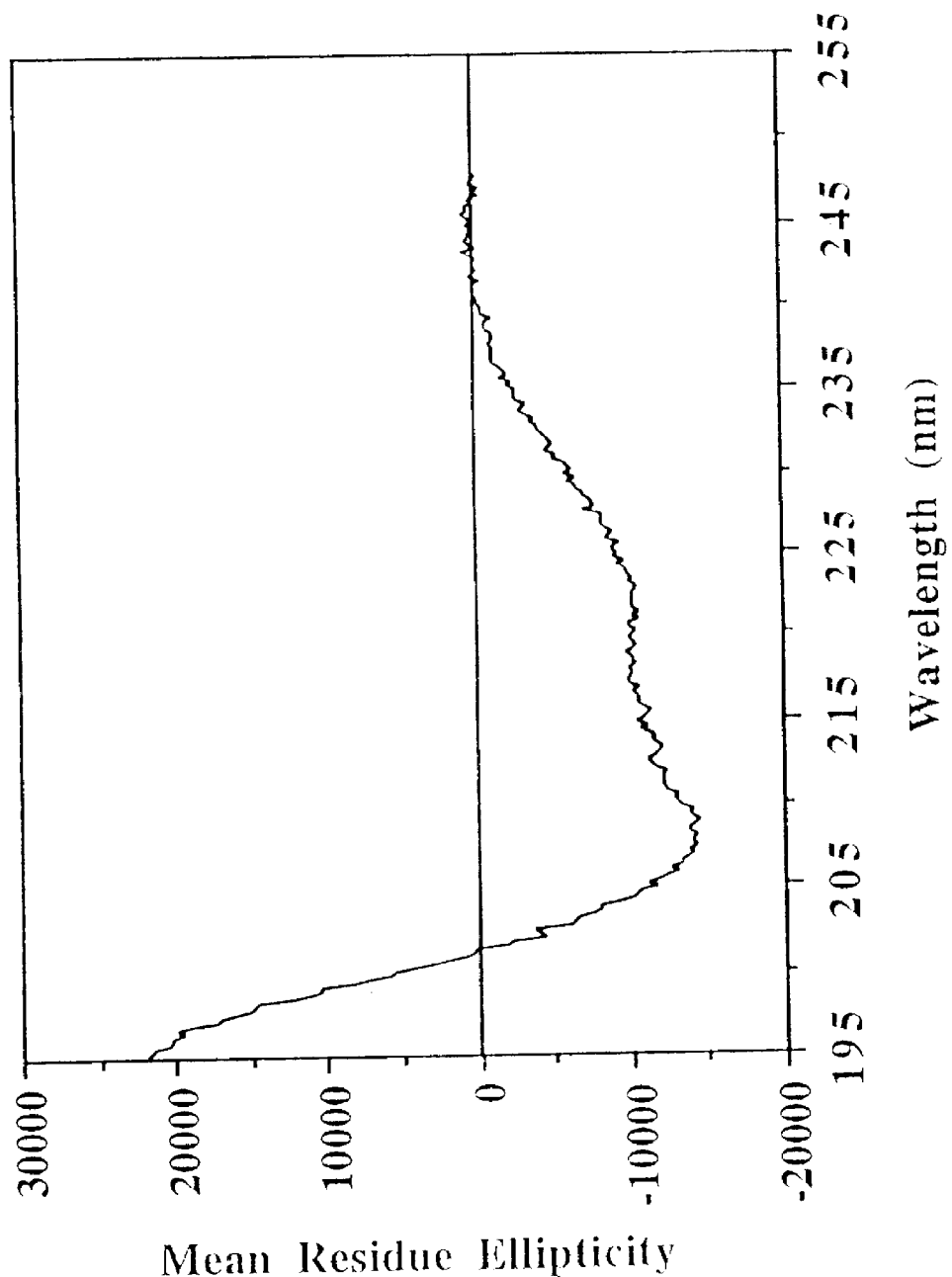
FIG. 5 shows the CD spectra of insulin extracted from 1-octanol using an aqueous solution of 0.10M HCl.

FIG. 4 shows the far ultraviolet CD spectrum of insulin extracted from 1-octanol into an aqueous solution of 0.10M HCl. The pathlength was 1 mm, the sample concentration 53 ug/ml, and the sample temperature 5° C. Upon shaking an octanol solution of insulin with an aqueous solution containing 0.10M HCl, insulin can be extracted back into the aqueous phase, presumably due to replacement of the SDS counterion with chloride. Lower HCl concentrations did not affect extraction of insulin from 1-octanol. Examination of the CD spectrum of the redissolved material (FIG. 4) indicates an overall structure similar to that of native insulin.

Example 8

Increased Thermal Stability of the SDS:Insulin Complex

Figure 6:
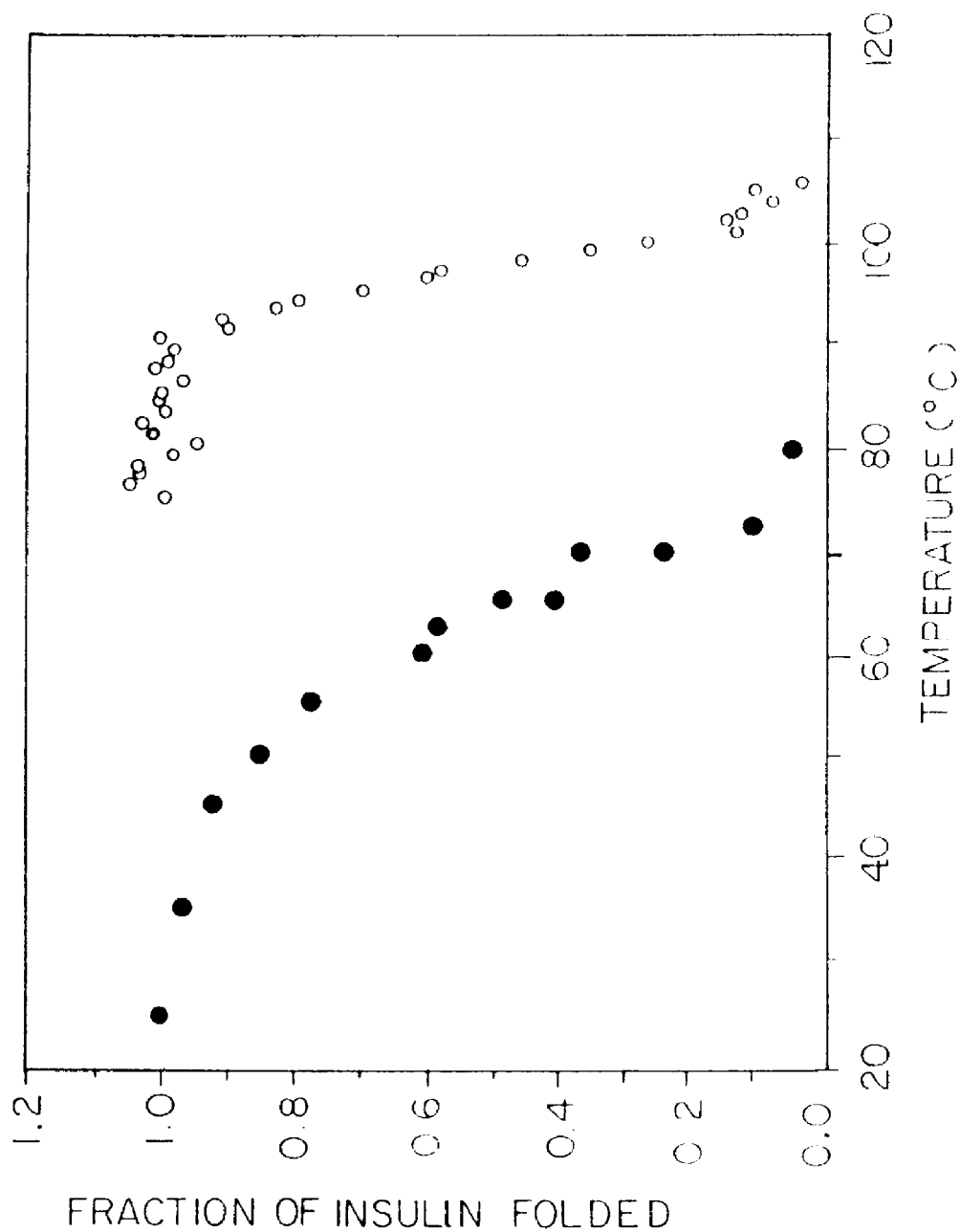
FIG. 6 shows the effect of temperature on the denaturation of insulin dissolved in 1-octanol.
Figure 9:
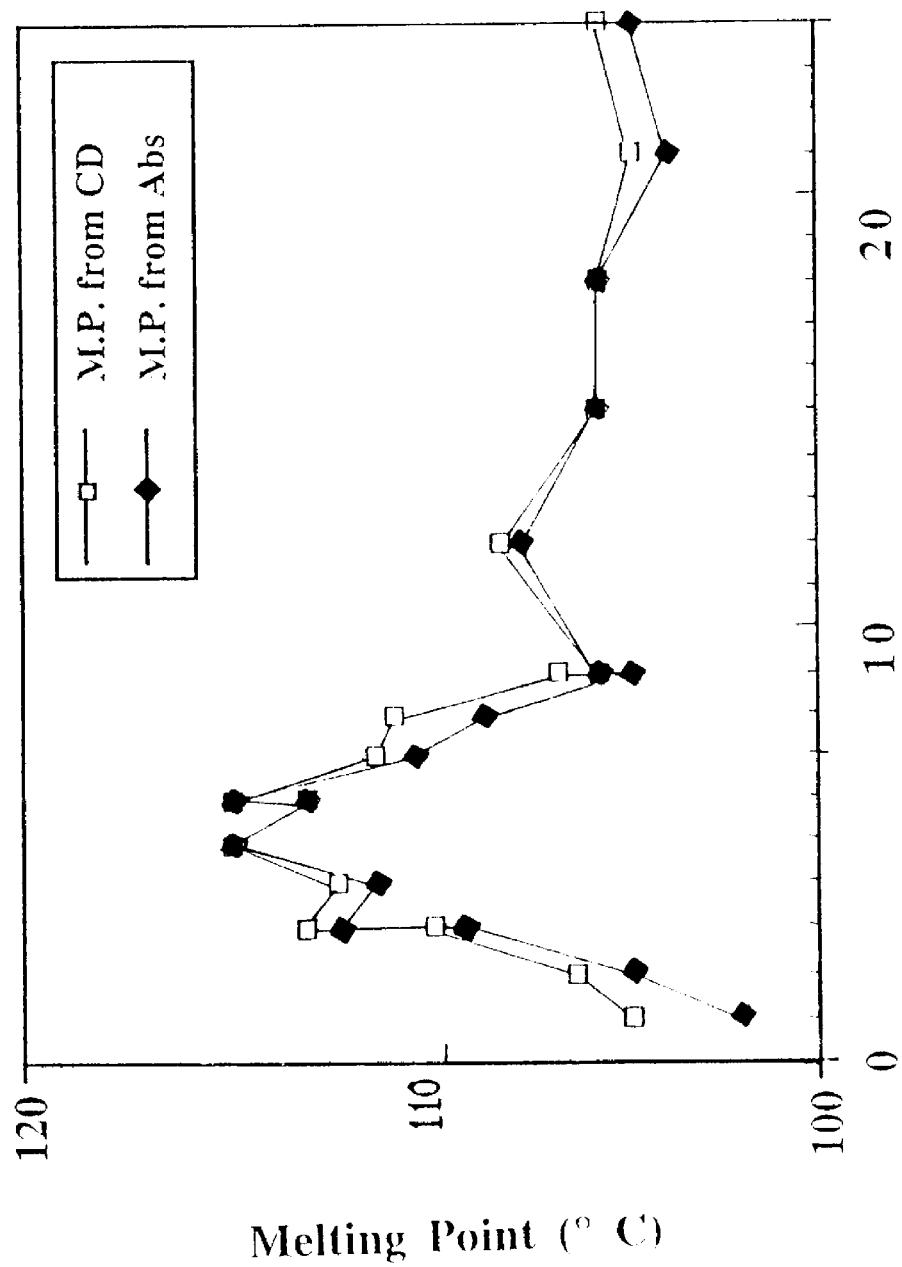
FIG. 9 shows the melting point of the SDS:insulin HIP complex as a function of the molar ratio of SDS to insulin.

The stability of insulin to thermal denaturation is difficult to assess as chemical degradation rates are rapid at elevated temperatures (Ettinger and Timasheff (1971) Biochemistry 10:824–831). In aqueous solution, the thermal denaturation of insulin occurs at a $T_m$ of about 65° C. [define $T_m$. The $T_m$ of insulin in 1-octanol has been measured, following molar ellipticity at 222 nm, to occur at 98° C. (FIG. 6), which is more than 30 degrees above that observed in water. This observation supports the conclusion that proteins dissolved in organic solvents demonstrate exceptional thermal stability. Although prior reports have observed that proteins suspended in organic solvents exhibit increased chemical stability due to lack of water (Ahern and Klibanov (1987) references), the present disclosure is the first report to find increased protein stability of the SDS:protein complex in organic solvent with respect to denaturation. Furthermore, as shown in FIG. 9, the SDS-insulin complex appears to maintain its native structure in 1-octanol, even after prolonged heating at 70° C. for more than 1 hour.

Example 9

Behavior of Large Proteins Complexed with SDS

Larger proteins can also form complexes with SDS. At pH 7.8, the aqueous solubility of human growth hormone (hGH) was not affected by addition of SDS, even at ratios of 100:1. However, at pH 2, hGH precipitates from aqueous solution at SDS ratios ranging from 10:1 to 40:1. At higher SDS concentrations, hGH redissolves, presumably via micellar solubilization. The hGH precipitate was not found to be soluble in 1-octanol, as determined by spectrophotometric assay. However, it was easily suspended in water and various oils, such as olive oil.

Example 10

Behavior of Bovine Pancreatic Tryosin Inhibitor Complexed with SDS

Figure 7:
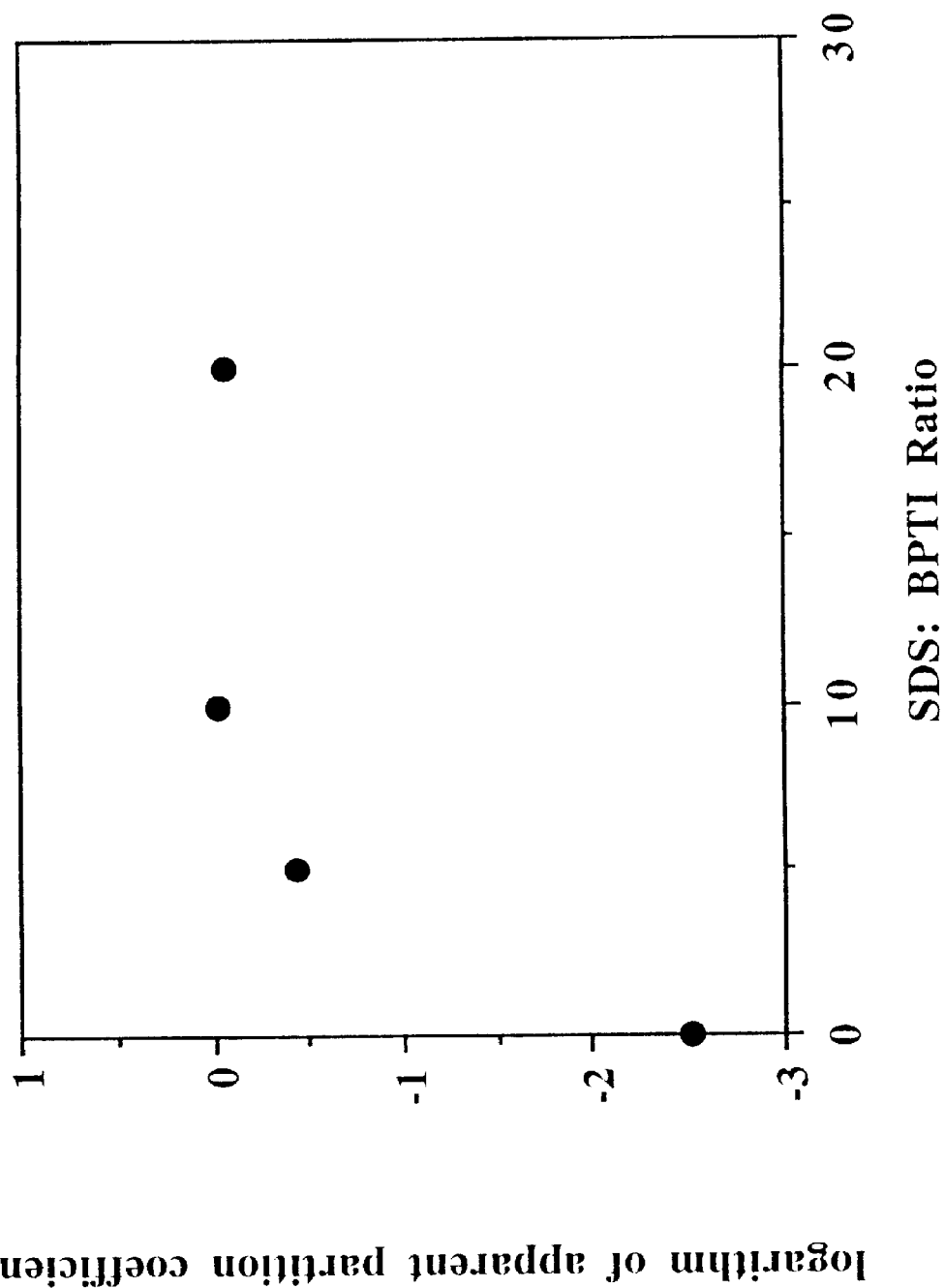
FIG. 7 shows the logarithm of the apparent partition coefficient of bovine pancreatic trypsin inhibitor (BPTI) from pH 4 water into 1-octanol.

Other proteins can also form complexes with SDS. Bovine pancreatic trypsin inhibitor (BPTI) is a small basic protein (MW 5900) with a well defined and stable structure (Wlodawer et al. (1984) J. Mol. Biol. 180:301–329, and (1987) J. Mol. Biol. 193:145–156). At pH 4, it partitions into 1-octanol upon addition of SDS (FIG. 7). As with insulin, the structure is maintained (data and shown) and the SDS-BPTI complex is soluble in other solvents as well, such as NMP and trimethyl phosphate (TMP). In TMP, the globular structure is compromised, as determined by CD spectroscopy. Apparently, TMP is a strong enough solvent to displace water from the hydration sphere and destabilize the structure of BPTI. This mechanism of protein denaturation has been described in detail by Arakawa and Timasheff (1982) Biochemistry 21:6536–6544, and (1982) Biochemistry 21:6545–6552.

Example 11

Behavior of HIP Complex Formation with Human Serum Albumin

Figure 8:
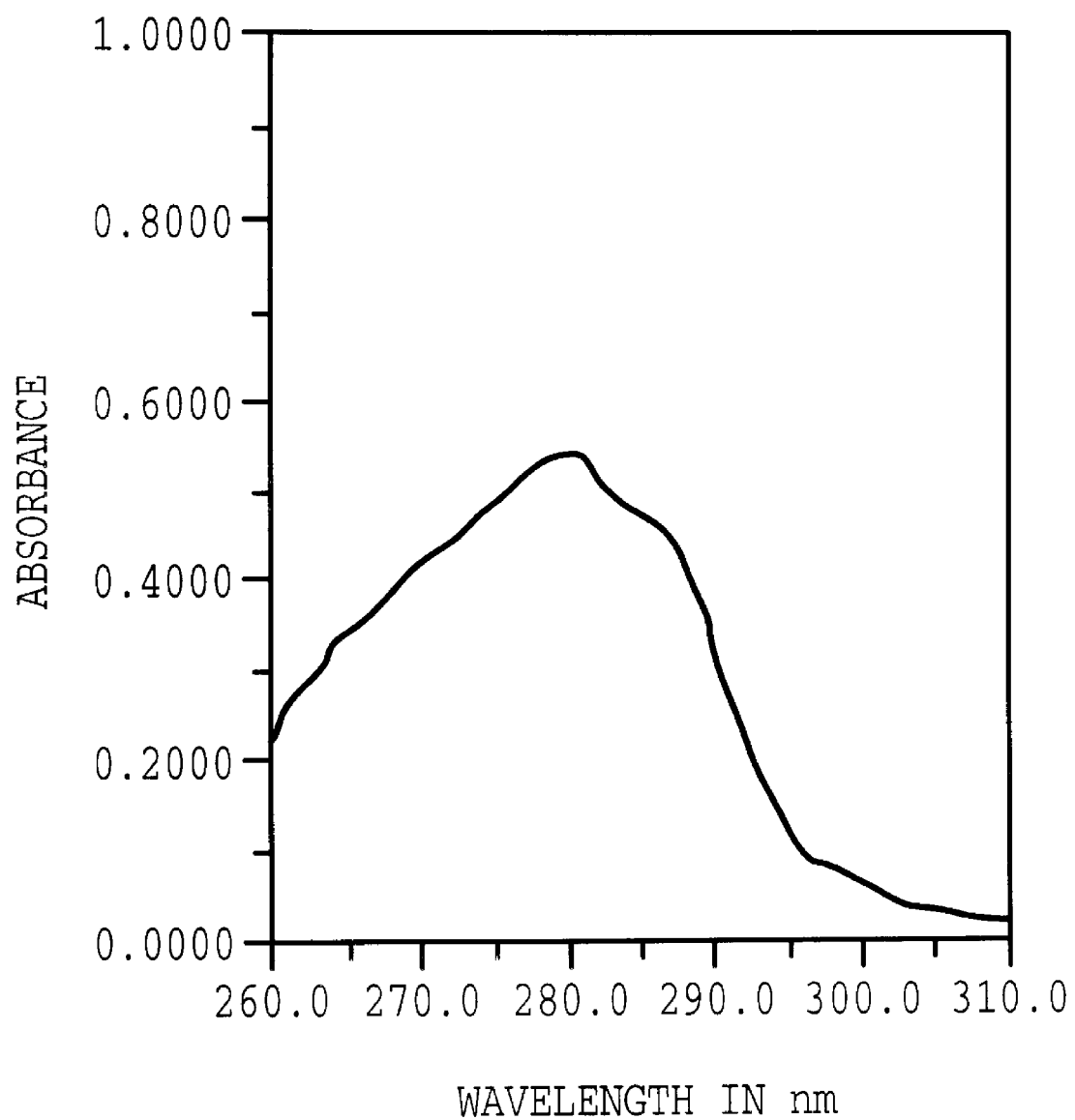
FIG. 8 shows the UV-visible absorption spectrum of human serum albumin (HSA) in NMP (50:1 SDS to HSA ratio).

Stoichiometric addition of SDS to human serum albumin (HSA) (MW 68 kD) produces precipitates as a hydrophobic ion pair complex is formed. While partitioning into 1-octanol could not be detected by UV-visible absorption spectroscopy, the SDS-HSA complex was found to be soluble in NMP (FIG. 8), yielding solutions of concentrations greater than 1 mg/ml (pathlength=1 cm, sample temperature=27° C.). Without SDS, the solubility of HSA in NMP is less than 0.03 mg/ml.

Example 12

Melting Point of SDS:Insulin Complex

The melting point (MP) of SDS:insulin ion pairs in 1-octanol was studied at SDS:insulin ratio ranging from 1:1 to 1:24.

Insulin at 1 mg/ml in 0.005N HCl was prepared containing SDS at 1, 2, 3, 4, 5, 6, 7, 8, 9, 12, 15, 18, 21 and 24 moles of SDS per mole of insulin. Equal volumes of octanol were added to each SDS:insulin solution to partition the insulin into the octanol phase. The concentration of the SDS:insulin complex extracted into the octanol was estimated by its absorbance at 278 nm and the solution diluted to 200 ug/ml. The melting point of the various insulin in octanol solutions was then determined with an AVIV 62DS circular dichroism spectrometer. Both circular dichroism (CD) signal and light scattering (as measured by changes in absorbance) were measured at 222 nm and the melting point determined by an inflection point in the measured scan.

FIG. 9 shows the graph of melting point as a function of SDS:insulin molar ratios, with an apparent maximum at 6:1 molar ratio and a melting point of about 116° C. The molar ratio of 6:1 is also the stoichiometric ratio and show the highest thermal stability for insulin in octanol.

Figure 10:
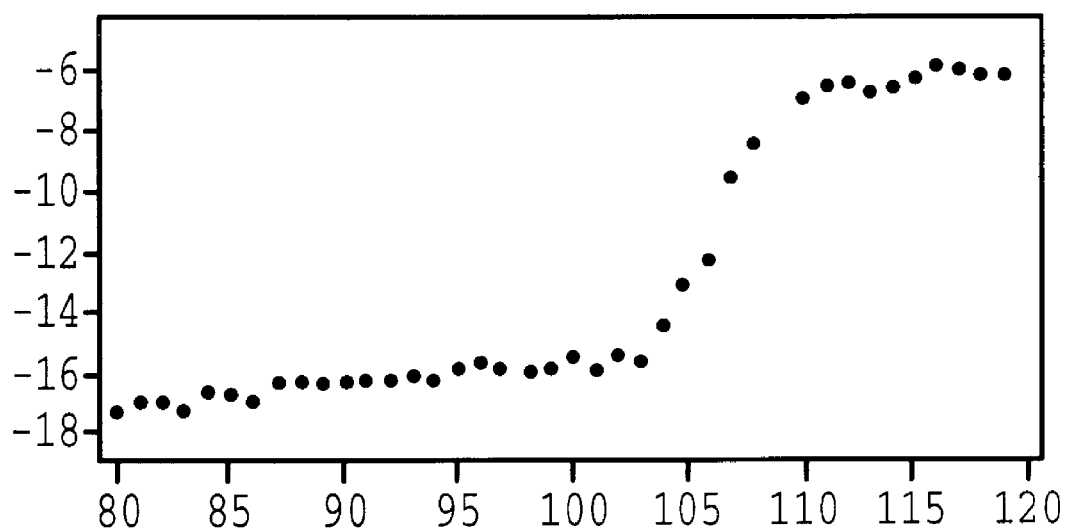
FIG. 10 shows a CD scan for a 9:1 SDS:insulin molar ratio at 222 nm as a function of temperature.
Figure 11:
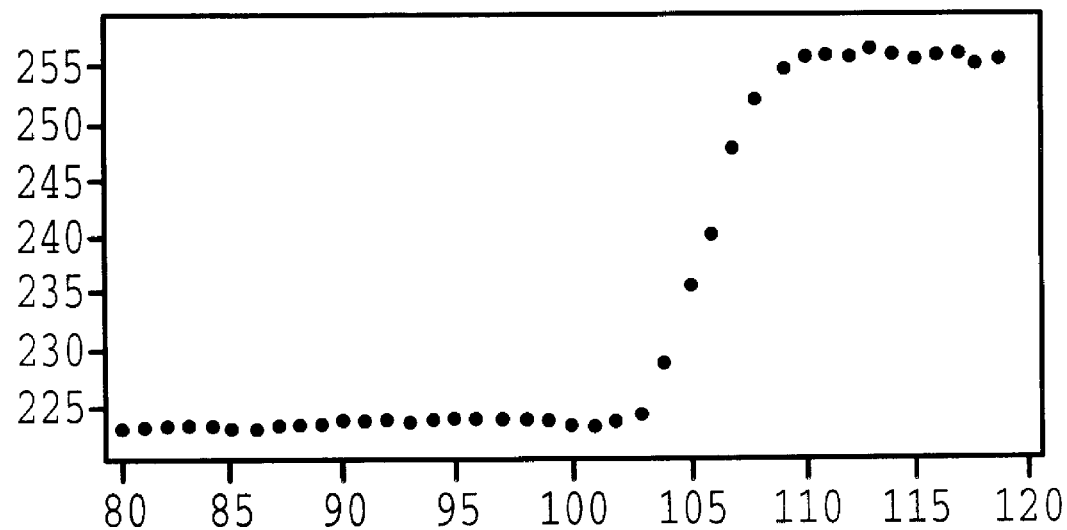
FIG. 11 shows an absorbance scan for a 9:1 SDS:insulin molar ratio at 222 nm as a function of temperature.

FIG. 10 shows a typical CD scan at 222 nm as a function of temperature. A melting point of 106° C. was determined by the maxima of the first derivative of the pictured data. FIG. 11 shows a typical absorbance scan at 222 nm as a function of temperature and effectively mimics the CD scan, showing a melting point of 106° C.

Example 13

Formation of a Fine Suspension HIP Complex for Pulmonary Delivery

Figure 13:
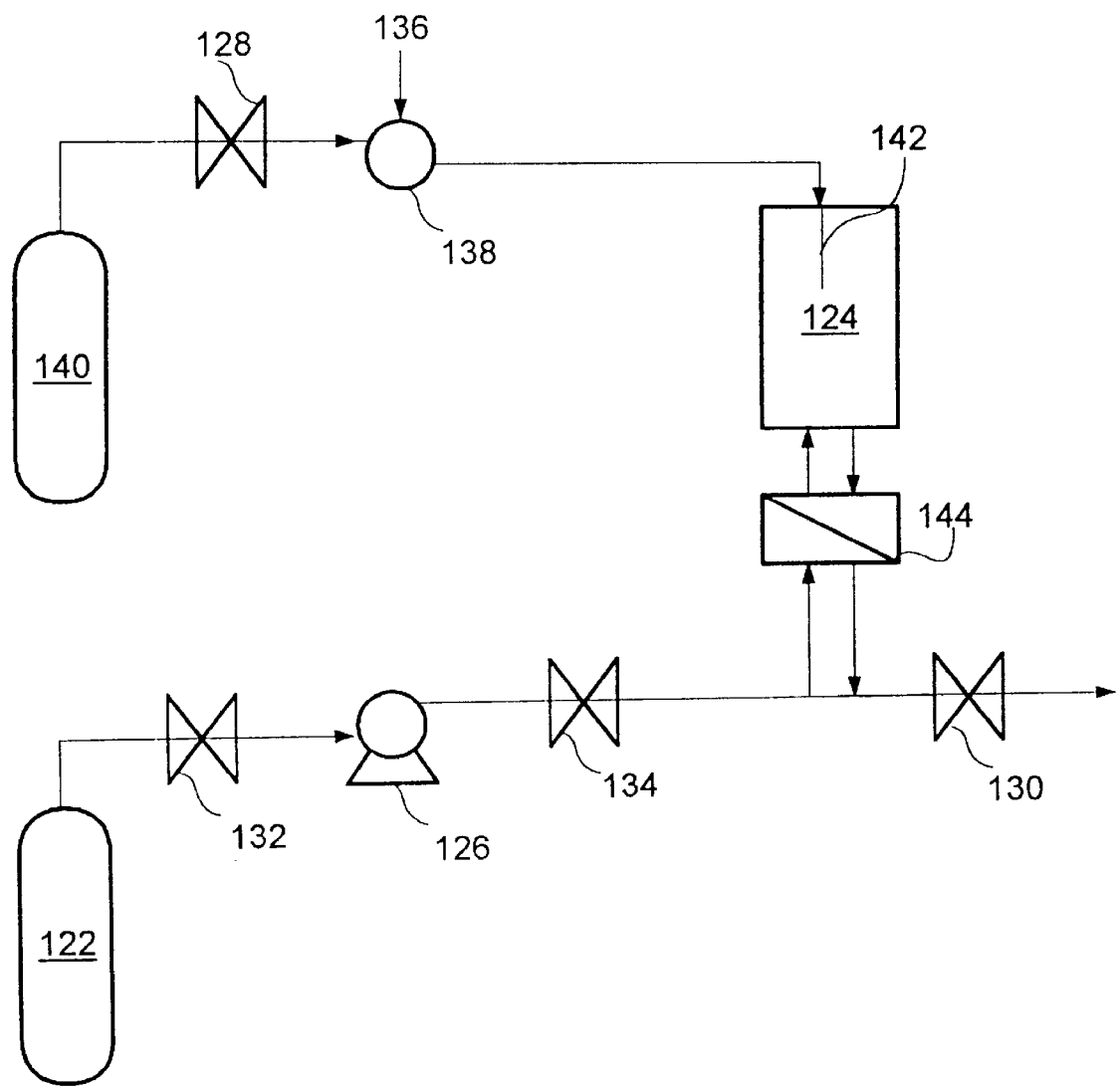
FIG. 13 shows a process flow diagram for batch processing for gas antisolvent precipitation relating to Examples 19–29.

For the formation of particles for pulmonary delivery, a protein solution is stirred vigorously using a homogenizer. SDS is added dropwise to the agitated solution. Particles in the 2–10 micron range are obtained. These particles are separated from the mixture by centrifugation or filtration. The particles are then suspended in a mixture of Freon® 11 and 12, such than when placed in a meter dose inhaler, a therapeutic amount of protein is delivered on each actuation.

Example 14

Uniform Distribution of Protein Throughout a Hydrophobic Polymer for Use in an Injectable Implant The biodegradable polymer consisting of a 50:50 mixture of poly-lactic acid and poly-glycolic acid is dissolved in a volatile organic solvent, such as N-methyl-pyrrolidone (NMP). An appropriate amount of an HIP-protein complex such as insulin-SDS (0.5%–5.0% by weight relative to the polymer) is dissolved in the same solvent. The two solutions are mixed and stirred for one hour. After the mixing is complete, the solvent is removed by evaporation. This is done in a mold to form an implant, or by a spray drying procedure to form small uniform particles for injection. The resulting solid material can also be ground to a powder and formulated as an injectable suspension. The protein is released from these systems as the polymer biodegrades and the HIP complex hydrolyses.

Example 15

Use of HIP Complex Formation for Protein Storage

The HIP complex is formed by dissolving the protein or polypeptide in water at minimal ionic strength. The pH is adjusted to as low a pH value as is practical to ensure stability and activity. A stock solution of SDS is added so that the number of equivalents of SDS matches the number of basic groups. For insulin, the pH is adjusted to 2.5, and 6 molar equivalents of SDS are used per mole of insulin. The resulting complex precipitates from solution, is collected, and dried at room temperature. The solid HIP complex may be stored at higher humidities and temperatures than the native proteins without noticeable loss of activity.

Dissolution in a non-reactive organic solvent, such as 1-octanol, produces a true solution of a protein. The HIP complex of insulin stored in 1-octanol is much more stable than insulin in water, as shown by its enhanced thermal stability.

Example 16

Use of HIP Complex Formation for Protein Purification

The hydrophobicities of HIP complexes of proteins will differ according to the fraction of the protein's surface covered by the alkyl sulfate molecules. In turn, the HIP protein complexes are separated using a variety of methods, including hydrophobic interaction columns.

Further, proteins may be purified by selective precipitation out of solution. For example, a protein is separated from additives such as human serum albumin (HSA), which may be present in amounts 20–50 times greater than the protein. Since HSA does not precipitate out of solution at pH 5.0 with SDS, a basic protein may be selectively precipitated and purified from HSA under those conditions.

Example 17

Use of HIP Complex Dissolved in an Organic Solution for Administration of a Protein to a Patient The administration of HIP complexes to a patient may be accomplished in a number of ways. A biodegradable polymer/HIP complex system may be dissolved in an organic solvent, for example N-methyl pyrrolidone, and injected subcutaneously to form an implant, processed to form microspheres which can be injected subcutaneously or intramuscularly, processed to form an implant which is placed surgically under the skin, or given orally as part of an oral delivery system for peptides and proteins. The solid HIP complex may also be prepared as a suspension or a non-aqueous solution, which may be injected or placed on the skin where the complex may partition into the skin. The HIP complex may also be nebulized and administered to a patient via inhalation, for pulmonary drug delivery. The HIP complex may also be formulated to be given orally, such that it is protected from degradation in the stomach via an enterically coated capsule, and released in either the upper or lower intestinal tract. The HIP complex may be loaded alone or in conjunction with oils, bile salts, or other enhancers to increase absorption. The HIP complex may also be suspended or dissolved in oil and introduced to the patient as a rectal or vaginal suppository.

Example 18

Preparation of a Drug With Reduced Bitter Taste

The low solubility of the HIP complex results in diminished taste of bitter tasting drugs taken orally. The HIP complex may also be dissolved in oil so as to further reduce bitter taste. The slow rate of hydrolysis, especially in an oil-type vehicle, prevents the bitter tasting drug from dissolving in the mouth and being tasted.

Examples 19–29

Batch Preparation of Particles Using Gas Antisolvent Precipitation

Examples 19–29 demonstrate batch manufacture of particles having a pharmaceutical substance and an amphiphilic material using supercritical carbon dioxide as a gas antisolvent.

FIG. 13 shows a process flow diagram for the batch processing of Examples 19–29. Referring to FIG. 13, supercritical carbon dioxide from the antisolvent tank 122 is fed into the antisolvent chamber 124 and is pressurized using a hand syringe pump 126, with valve 128 and valve 130 closed and valve 132 and valve 134 open. After the antisolvent chamber is pressurized, then valve 134 is closed and the test solution 136 is fed into an injection port 138. Nitrogen from a propellant tank 140 is pressurized behind the injection port 138 and is used to force the solution through a sonicated orifice 142 to spray the test solution 136 into the antisolvent chamber 124. The test solution 136 for each example has a pharmaceutical substance and an amphiphilic material dissolved together as a hydrophobic ion pair complex in an organic solvent. Some examples have a biodegradable polymer also dissolved in the organic solvent. Solid particles which precipitate are allowed to settle, with all valves closed, onto a scanning electron microscope (SEM) stub in the antisolvent chamber 124. The antisolvent chamber 124 is then slowly depressurized through the valve 130 and the SEM stub is removed for analysis. Any remaining solid particles from the antisolvent chamber 124 are collected on the filter 144.

Figure 14:
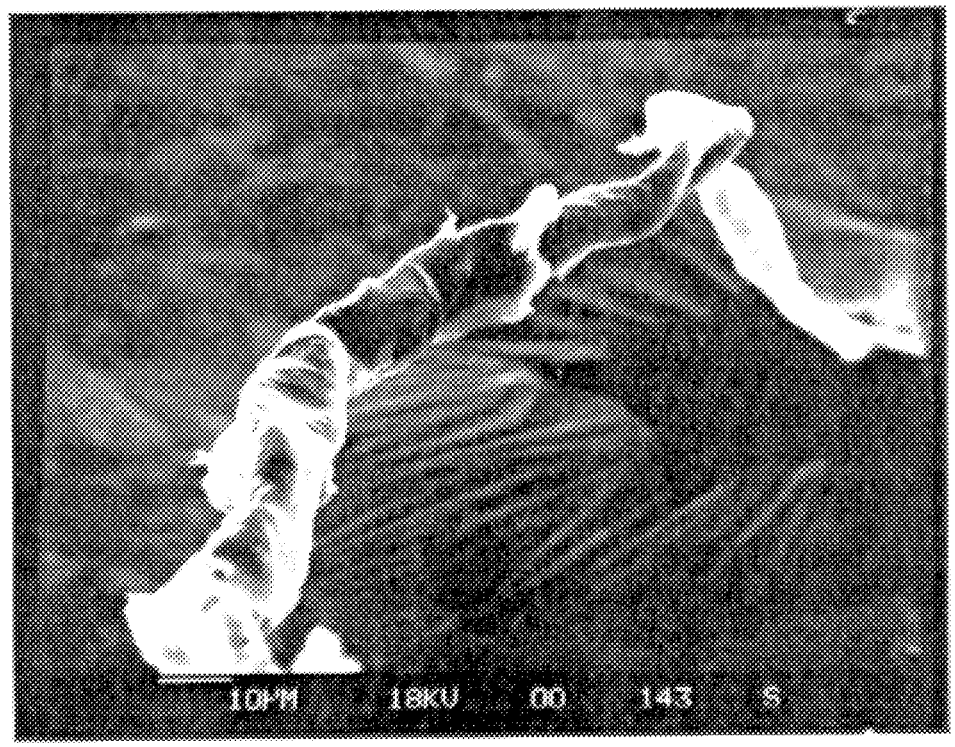
FIG. 14 is an SEM photomicrograph of a particle of the present invention comprising imipramine.
Figure 15:
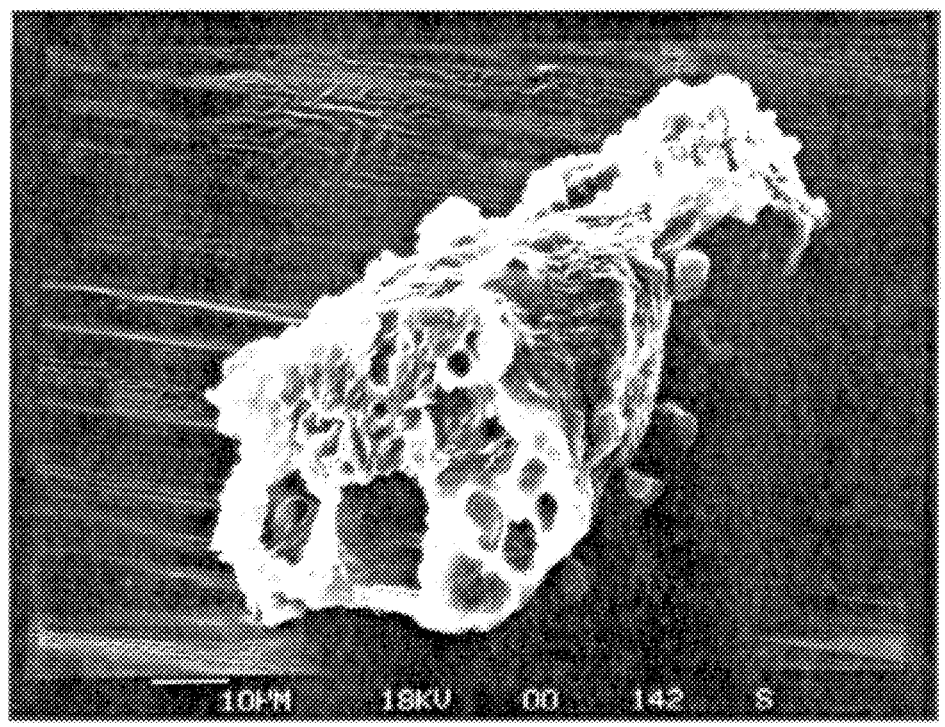
FIG. 15 is another SEM photomicrograph of a particle of the present invention comprising imipramine.
Figure 16:
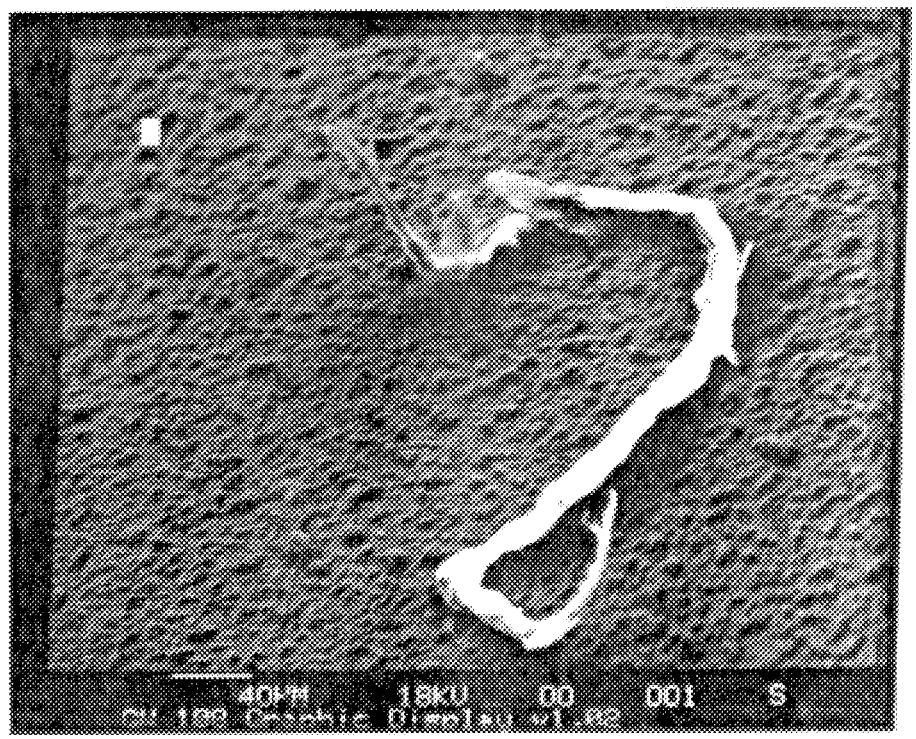
FIG. 16 is a SEM photomicrograph of a particle of the present invention comprising ribonuclease and poly (ethyleneglycol).
Figure 17:
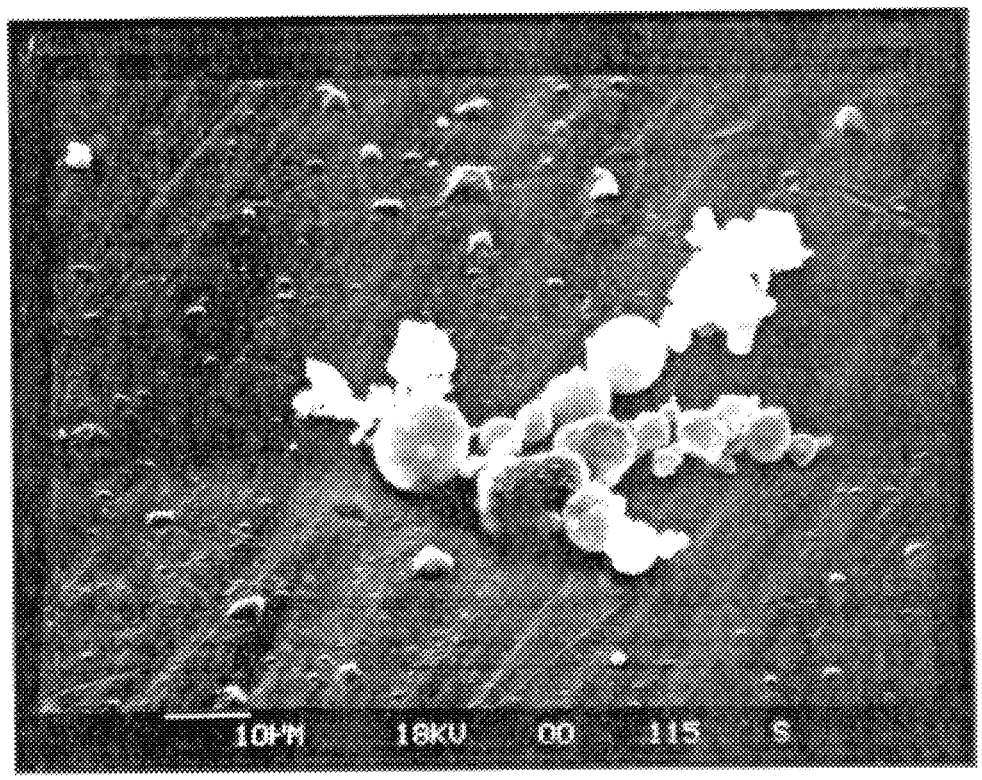
FIG. 17 is a SEM photomicrograph of particles of the present invention comprising α-chymotrypsin.
Figure 18:
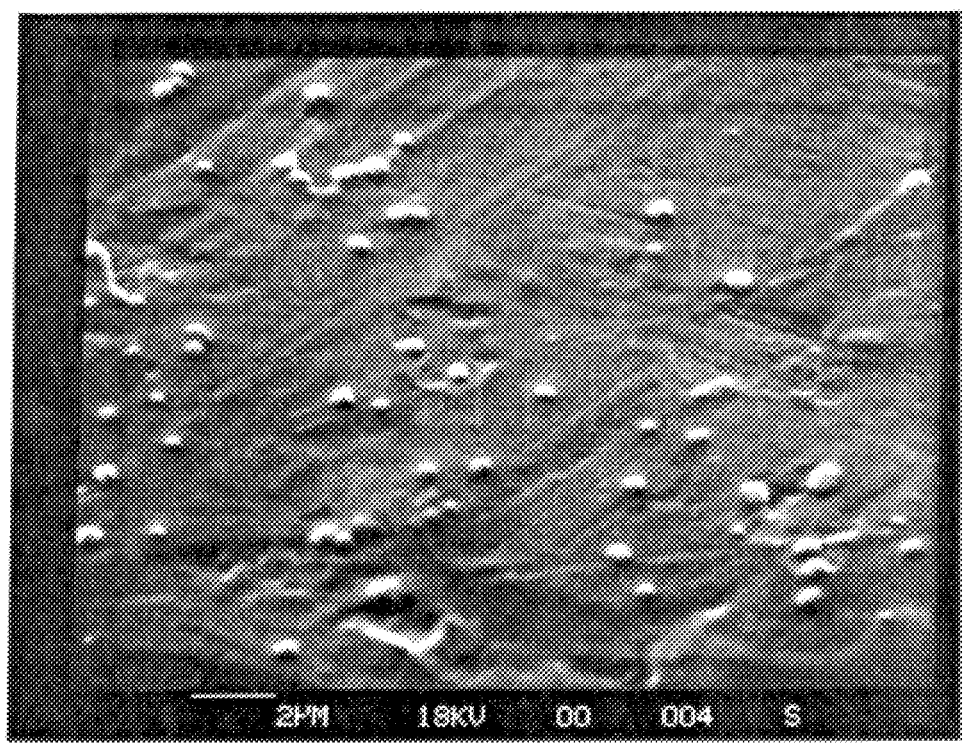
FIG. 18 is a SEM photomicrograph of particles of the present invention comprising pentamidine.

The makeup of each test solution for Examples 19–29 is shown in Table 2. Test conditions and results, including a description of particles which are precipitated, are shown in Table 3. FIGS. 14 and 15 are SEM photomicrographs of imipramine particles of Example 22, showing the elongated fiber-like shape of the particles. In FIG. 15 it may be seen that the fiber-like particle has a hollow interior in which small particles of another pharmaceutical substance could be loaded for some pharmaceutical applications. FIG. 16, is a SEM photomicrograph of a particle of ribonuclease and poly(ethylene glycol) of Example 27, showing an opening in the end of the particle into a hollow interior space. FIG. 17 is a SEM photomicrograph of particles of α-chymotrypsin of Example 19, showing ultrafine spheroidal particles of a size smaller than about 10 microns, with many of a size of around 1 micron. FIG. 18 is a SEM photomicrograph of pentamidine particles of Example 29 of a size smaller than about 1 micron.

TABLE 3

| Example | Test Conditions Temp (°C.) | Press. (bar) | Particles |
|---|---|---|---|
| 19 | 34 | 76 | spheroidal, approx. 10μ and smaller |
| 20 | 28 | 76 | irregular shape, approx. 1μ dia. |
| 21 | | | spheroidal, approx. 2–3μ dia. |
| 22 | 36 | 85 | fiber-like, approx. 10μ dia. and 1 cm long |
| 23 | 34.5 | 85 | spheroidal |
| 24 | 34.6 | 85 | irregular, approx. 1–5μ |
| 25 | 35.2 | 85 | |
| 26 | 35.5 | 85.5 | spheroidal, approx 50μ |
| 27 | 35.3 | 85 | fiber-like, approx. 10μ dia. and 1 mm long, spheroidal, approx 0.5–1μ |
| 28 | 35.3 | 77 | collapsed spheres, approx 5μ dia. |
| 29 | 35 | 82 | spheroidal, approx. 0.1–1μ dia. |

Examples 30–32

Continuous Manufacture of Solid Particles by Gas Antisolvent Precipitation

Examples 30–32 show continuous manufacture of solid particles comprising a pharmaceutical substance and an amphiphilic material.

Figure 19:
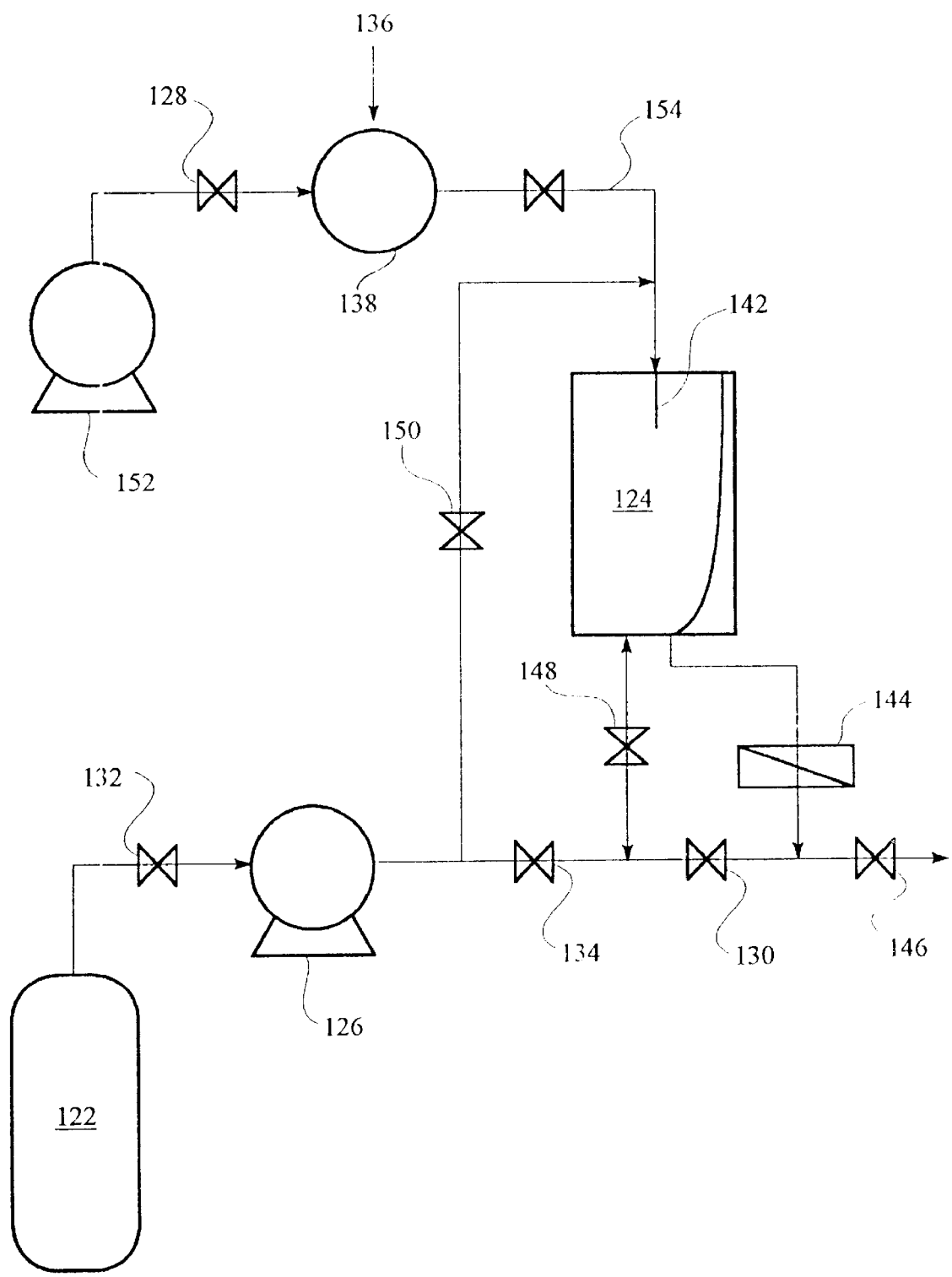
FIG. 19 shows a process flow diagram for continuous processing for gas antisolvent precipitation relating to Examples 30–32.

FIG. 19 shows a process flow diagram for the continuous manufacture test for Examples 30–32. The antisolvent chamber 124 is first pressurized with an automatic syringe pump 126 with a back pressure regulator 146 adjusted to maintain the desired antisolvent pressure in the antisolvent chamber 124 at a given antisolvent flow rate through the system. This initial pressurization is performed with the valve 148, the valve 134 and the valve 130 closed and with

TABLE 2

| | Pharm. Substance | | Amph. Material | | Polymer | | |
|---|---|---|---|---|---|---|---|
| Example | Type | Conc.[1] | Type | Ratio[2] | Type | Conc.[3] | Solvent |
| 19 | α-chymotrypsin | 1.4 | AOT[4] | 40 | — | — | iso-octane |
| 20 | α-chymotrypsin | 3.81 | AOT[4] | 40 | — | — | iso-octane |
| 21 | α-chymotrypsin | 0.1 | AOT[4] | 40 | PLA[5] | 1.31 | methylene chloride |
| 22 | Imipramine | 3.4 | AOT[4] | 1 | — | — | iso-octane |
| 23 | Insulin | 1.33 | SDS | 9 | — | — | pyridine |
| 24 | Insulin | 1.33 | SDS | 9 | — | — | THF[8] |
| 25 | Insulin | 1.33 | SDS[6] | 9 | — | — | methanol |
| 26 | Ribonuclease | 1.0 | SDS[6] | 20 | — | — | methanol |
| 27 | Ribonuclease | 1.0 | SDS[6] | 20 | PEG[7] | 7.91 | methanol |
| 28 | cytochrome C | 0.23 | SDS[6] | 40 | — | — | ethanol |
| 29 | Pentamidine | 5.6 | SDS[6] | 2 | — | — | ethanol |

[1] mg of pharmaceutical substance per ml of solvent.
[2] molar ratio of amphiphilic material to pharmaceutical substance.
[3] mg of polymer per ml of solvent.
[4] bis-(2-ethylhexyl) sodium sulfosuccinate.
[5] poly(L-lactic acid) of approx. 100 KDa molecular weight.
[6] sodium dodecyl sulfate.
[7] poly(ethylene glycol) of approx. 3350 Da molecular weight.
[8] tetrahydrofuran the valve 150 and the valve 132 open. One of two methods for metering the solution 136 into the antisolvent chamber 124 is used for each example. One method is to load the pump 152 with pure solvent and to spray the pure solvent into the antisolvent chamber 124 until a steady state is achieved. The solution 136 is then loaded into the injection port 138 and spiked into the solvent delivery line 154 to the antisolvent chamber 124. The second method is to load the pump 152 with the solution and, bypassing the injection port, to deliver the solution to the antisolvent chamber 124. Both delivery techniques are operated at a flow rate of 1 milliliter per minute with a carbon dioxide flow rate of 20 milliliters per minute. In both cases, the solution enters the antisolvent chamber 124 through the sonicated orifice 142. During operation, carbon dioxide is vented from the top of the antisolvent chamber to allow particles to settle and not be entrained in the exiting carbon dioxide. Any particles that are washed out of the antisolvent chamber 124 are collected on the filter 144.

After spraying the solution 136 into the antisolvent chamber, then valves 150 and 130 are closed and valves 134 and 148 are opened and carbon dioxide is metered into the antisolvent chamber 124 from bottom to top to flush any residual solvent from the antisolvent chamber 124. The system is then slowly depressurized and particles which have precipitated are collected from either the antisolvent chamber 124 or the filter 144.

The makeup of the solution for each of Examples 30–32 is shown in Table 4. Table 5 shows the test conditions for each of Examples 30–32 and results of the examples, including a description of particles which are produced.

TABLE 4

| | Pharm. Substance | | Amph. Material | | Polymer | | |
|---------|------------|-----------|--------|--------|--------|-----------|-------------------|
| Example | Type | Conc.[1] | Type | Ratio[2] | Type | Conc.[3] | Solvent |
| 30 | streptomycin | 5 | AOT[4] | 3 | — | — | methylene chloride |
| 31 | streptomycin | 0.14 | AOT[4] | 3 | PLA[5] | 2.62 | methylene chloride |
| 32 | streptomycin | 0.66 | AOT[4] | 3 | PLA[5] | 2.62 | methylene chloride |

[1]mg of pharmaceutical substance per ml of solvent.
[2]molar ratio of amphiphilic material to pharmaceutical substance.
[3]mg of polymer per ml of solvent.
[4]bis-(2-ethylhexyl) sodium sulfosuccinate.
[5]poly(L-lactic acid) of 100 KDa molecular weight.

TABLE 5

| | Test Conditions | | |
|---------|-----------|--------------|-------------------------|
| Example | Temp (°C.) | Press. (bar) | Particles |
| 30 | 35 | 88 | spheroidal, approx. 1μ |
| 31 | 36.8 | 89 | spheroidal, approx. 0.4μ |
| 32 | 36.2 | 88.2 | spheroidal, approx. 0.4μ |

While various embodiments of the present invention have been described in detail, it should be understood that any feature of any embodiment may be combined with any other feature of any other embodiment. Any compatible combination of pharmaceutical substance, amphiphilic material, polymer and/or solvent may be used. Also, any feature of any processing method may be used with any solvent. Furthermore, the hollow, fiber-like particles may be prepared for any suitable combination of pharmaceutical substance and amphiphilic material. Moreover, the tubular-shaped particles may be made of a biodegradable polymer, alone or in combination with other materials, or a pharmaceutical substance, alone or in combination with other materials, which are directly soluble in the organic solvent. Such features are expressly included within the scope of the present invention.

Also, while various embodiments of the present invention have been described in detail, it is apparent that modifications and adaptations of those embodiments will occur to those skilled in the art. It is to be expressly understood, however, that such modifications and adaptations are within the scope of the present invention, as set forth in the following claims.

What is claimed is:

1. A method for making particles including a pharmaceutical material, which particles may be recovered in a powder form desirable for use in some pharmaceutical delivery methods such as inhalation for direct pulmonary delivery and injection in a slurry form, the method comprising the steps of:

forming solid particles comprising a pharmaceutical substance from a liquid solution, which particles could be recovered in powder form;

said liquid solution comprising said pharmaceutical substance and an amphiphilic material in solution in a carrier liquid wherein, said pharmaceutical substance, alone, is substantially not soluble in said carrier liquid and said amphiphilic material is capable of interacting with said pharmaceutical substance such that said pharmaceutical substance, in combination with said amphiphilic material as a hydrophobic ion pair complex, is present in a true, homogeneous solution in said carrier liquid prior to said step of forming said solid particles.

2. The method of claim 1, wherein
said pharmaceutical substance and said amphiphilic material, in said liquid solution, are associated in the form of a hydrophobic ion pair complex, which complex is soluble in said carrier liquid and is dissolved in said carrier liquid in the form of a true homogeneous solution.

3. The method of claim 1, wherein
said amphiphilic material, in said liquid solution, is present at a concentration at which substantially no micelles involving said amphiphilic material and substantially no reverse micelles involving said amphiphilic material are present in said liquid solution.

4. The method of claim 1, wherein
said amphiphilic material is selected from the group consisting of bis(2-ethylhexyl) sodium sulfosuccinate, sodium dodecyl sulfate, cholesterol sulfate, sodium laurate, and ionic forms and dissociation products of the foregoing.

5. The method of claim 1, wherein greater than 90 weight percent of said solid particles are smaller about 10 microns in size.

6. The method of claim 1, wherein greater than 90 weight percent of said solid particles are smaller than 6 microns in size.

7. The method of claim 1, wherein greater than 90 weight percent of said solid particles are in a size range of from 1 micron to 6 microns.

8. The method of claim 1, wherein greater than 90 weight percent of said solid particles are smaller than 1 micron in size.

9. The method of claim 1, wherein the method further comprises recovering said solid particles as a substantially dry powder.

10. The method of claim 1, wherein said solid particles comprise said amphiphilic material, in addition to said pharmaceutical substance.

11. The method of claim 10, wherein said solid particles comprise said pharmaceutical substance and said amphiphilic material in the form of a hydrophobic ion pair complex involving said pharmaceutical substance and said amphiphilic material.

12. The method of claim 1, wherein an antisolvent fluid is provided under conditions at which said antisolvent fluid and said carrier liquid are at least partially miscible and at which said pharmaceutical substance is substantially not soluble in said antisolvent fluid; and said step of forming said solid particles comprises contacting said liquid solution with said antisolvent fluid to cause said solid particles to form.

13. The method of claim 12 wherein said step of forming said solid particles comprises contacting said liquid solution with said antisolvent fluid under conditions which are supercritical or near critical relative to said antisolvent fluid.

14. The method of claim 12, wherein during said step of forming said solid particles, said liquid solution is contacted with said antisolvent fluid under thermodynamic conditions at which said antisolvent fluid is at a reduced pressure of greater than 0.5, relative to the critical pressure of said antisolvent fluid.

15. The method of claim 1, wherein said liquid solution further comprises a biodegradable polymer which is dissolved in said carrier liquid; and said solid particles comprise said biodegradable polymer, in addition to said pharmaceutical substance.

16. The method of claim 15, wherein said biodegradable polymer comprises at least some repeating units representative of polymerizing at least one of the following: an alpha-hydroxycarboxylic acid, a cyclic diester of an alpha-hydroxycarboxylic acid, dioxanone, a lactone, a cyclic carbonate, a cyclic oxalate, an epoxide, a glycol and an anhydride.

17. The method of claim 15, wherein said biodegradable polymer comprises at least some repeating units representative of polymerizing at least one of the following: lactic acid, glycolic acid, lactide, glycolide, ethylene glycol and ethylene oxide.

18. The method of claim 1, wherein said solid particles have an elongated, fiber-like shape.

19. The method of claim 18, wherein said solid particles have a hollow interior extending longitudinally within said solid particles.

20. The method of claim 18, wherein said particles have a diameter of smaller than 50 microns.

21. The method of claim 18, wherein said solid particles have a length of 0.5 millimeters to 1 centimeter.

22. The method of claim 1, wherein said amphiphilic material comprises a molecular structure having a hydrophilic portion and a hydrophobic portion, and wherein said hydrophilic portion is ionic.

23. The method of claim 22 wherein said hydrophilic portion is anionic.

24. The method of claim 22, wherein said amphiphilic material is selected from the group consisting of a sulfonate, a sulfate, a phosphate, a carboxylate, a sulfosuccinate and ionic forms and dissociation products of the foregoing.

25. The method of claim 22, wherein said hydrophilic portion is cationic.

26. The method of claim 22, wherein said amphiphilic material comprises at least one of an ammonium group, a guadininium group and substituted variations of the foregoing groups.

27. The method of claim 1, wherein said pharmaceutical substance is directly soluble in an aqueous liquid at a physiological pH and exhibits a charged character when dissolved in an aqueous liquid at a physiological pH.

28. The method of claim 27, wherein said pharmaceutical substance comprises a protein.

29. The method of claim 27, wherein said pharmaceutical substance comprises a polypeptide.

30. The method of claim 27, wherein said pharmaceutical substance comprises at least one of: ($\alpha$-chymotrypsin, ribonuclease, DNase, cytochrome, lypopressin, vasopressin, oxytocin, insulin, calcitonin gene-related peptide, LHRH agonists, ACTH, Gly-Phe-$NH_2$ dipeptide, bovine pancreatic trypsin inhibitor, human serum albumin, leuprolide, neurotensin, bradykinin, and human growth hormone.

31. The method of claim 27, wherein said pharmaceutical substance comprises an analgesic.

* * * * *